US010172541B2

(12) United States Patent
Liao et al.

(10) Patent No.: US 10,172,541 B2
(45) Date of Patent: Jan. 8, 2019

(54) MOTION RECOGNITION DEVICE AND METHOD

(71) Applicant: J-MEX Inc., Hsinchu (TW)

(72) Inventors: Wen-Hsuan Liao, Hsinchu (TW);
Chi-hung Chen, Hsinchu (TW);
Meng-Yu Lee, Hsinchu (TW);
Chao-Ling Chen, Hsinchu (TW);
Chih-Hung Hsu, Hsinchu (TW);
Chi-Hung Hsieh, Hsinchu (TW);
Chun-Yuan Huang, Hsinchu (TW);
Deng-Huei Hwang, Hsinchu (TW);
Kun-Ming Tsai, Hsinchu (TW);
Tsang-Der Ni, Hsinchu (TW); I-Tang Chen, Hsinchu (TW); Kwang-Sing Tone, Hsinchu (TW)

(73) Assignee: J-MEX INC., Hsinchu (TW)

( * ) Notice: Subject to any disclaimer, the term of this patent is extended or adjusted under 35 U.S.C. 154(b) by 330 days.

(21) Appl. No.: 15/015,575

(22) Filed: Feb. 4, 2016

(65) Prior Publication Data
US 2017/0086711 A1 Mar. 30, 2017

Related U.S. Application Data

(60) Provisional application No. 62/232,761, filed on Sep. 25, 2015.

(51) Int. Cl.
*A61B 5/11* (2006.01)
(52) U.S. Cl.
CPC .......... *A61B 5/1123* (2013.01); *A61B 5/1118* (2013.01); *A61B 5/1126* (2013.01)

(58) Field of Classification Search
CPC ... A61B 5/1036; A61B 5/1123; A61B 5/1118; A61B 5/1126; A61B 5/00; A61B 5/1038; G06F 3/00
(Continued)

(56) References Cited

U.S. PATENT DOCUMENTS 8,260,384 B2 9/2012 Wulff
8,475,370 B2 * 7/2013 McCombie .......... A61B 5/0002
600/301

(Continued)

OTHER PUBLICATIONS

Written Opinion mailed in corresponding International Patent Application No. PCT/US2016/053307 dated Dec. 8, 2016, consisting of 42 pp.

(Continued)

*Primary Examiner* — Jonathan Dunlap
*Assistant Examiner* — Octavia Hollington
(74) *Attorney, Agent, or Firm* — Volpe and Koenig, P.C.

(57) ABSTRACT

A motion recognition device includes a sensing unit and a processing unit. The sensing unit generates a sense signal in response to a body motion occurring at a specific position on a user's body, wherein the sense signal includes a first sense signal portion and a second sense signal portion different from the first sense signal portion, and the body motion belongs to a motion segment of a motion type. The processing unit processes the sense signal to generate a motion parameter signal structure including a fusion signal of the first and the second sense signal portions, and recognizes the specific position to determine an effective reference signal for recognition of the motion type based on the motion parameter signal structure.

18 Claims, 15 Drawing Sheets

(58) Field of Classification Search
USPC .......................................................... 73/865.4
See application file for complete search history.

(56) References Cited

U.S. PATENT DOCUMENTS

| | | | |
|---|---|---|---|
| 8,783,122 B2* | 7/2014 | Klose | A61B 5/1118 |
| | | | 73/865.4 |
| 8,787,006 B2 | 7/2014 | Golko | |
| 9,582,072 B2* | 2/2017 | Connor | G06F 3/011 |
| 9,782,104 B2* | 10/2017 | MacEachern | A61B 5/0488 |
| 9,891,718 B2* | 2/2018 | Connor | G06F 3/017 |
| 2003/0208335 A1 | 11/2003 | Unuma | |
| 2008/0054039 A1 | 3/2008 | Wulff | |
| 2008/0214360 A1* | 9/2008 | Stirling | A61B 5/1038 |
| | | | 482/9 |
| 2008/0262392 A1 | 10/2008 | Ananny | |
| 2012/0194976 A1 | 8/2012 | Golko | |
| 2013/0044215 A1 | 2/2013 | Rothkopf | |
| 2014/0172873 A1 | 6/2014 | Varoglu | |
| 2014/0336947 A1 | 11/2014 | Walke | |
| 2015/0164377 A1* | 6/2015 | Nathan | A61B 5/1122 |
| | | | 600/595 |

OTHER PUBLICATIONS

International Search Report mailed in corresponding International Patent Application No. PCT/US2016/053307 dated Dec. 8, 2016, consisting of 2 pp.

* cited by examiner

MOTION RECOGNITION DEVICE AND METHOD

CROSS-REFERENCE TO RELATED APPLICATION AND CLAIM OF PRIORITY

The application claims the benefit of U.S. provisional patent application Ser. No. 62/232,761 entitled "MOTION RECOGNITION DEVICE AND METHOD", filed on Sep. 25, 2015, the disclosures of which are incorporated herein in their entirety by reference.

TECHNICAL FIELD

The present disclosure is related to a recognition device and method and, more particularly, is related to a motion recognition device and method.

BACKGROUND

The main function of a conventional motion-sensing device is to generate a reciprocating signal by sensing a motion, and interpret the reciprocating signal to count the reciprocating times of the motion. The most chief representative product on the market is a pedometer; however, this type of sensing device cannot recognize the motion type or the motion mode, and can only purely count the motion cycles of the motion. Because the conventional motion-sensing device has the abovementioned operational characteristic, the availability that the wearable motion-sensing device is employed to recognize various motion types is restricted.

U.S. Pat. No. 8,260,384 B2 discloses a wearable mobile computing system. U.S. Patent Publication No. 2014/0336947 A1 discloses a method and device for mobile training data acquisition and analysis of strength training U.S. Pat. No. 8,787,006 B2 discloses a wrist-worn electronic device and methods therefor. U.S. Patent Publication No. 2008/0262392 A1 discloses calibration techniques for activity sensing devices. U.S. Patent Publication No. 2013/0044215 A1 discloses a bi-stable spring with a flexible display. U.S. Patent Publication No. 2014/0172873 A1 discloses a method and apparatus for personal characterization data collection using sensors.

SUMMARY OF EXEMPLARY EMBODIMENTS

It is appropriate for a motion-sensing device to clearly recognize multiple motion characteristics so as to definitely distinguish one motion type from other motion types and report the recognition results to the physical exerciser; in this way, the physical exerciser is effectively aided to achieve the health effects. For instance, there are three motion types, performed by the physical exerciser, belonging to the same motion type group. The three motion types may have similar motions. When physical exercisers do the three motion types in different exercise modes or habits, the muscle shapes formed by the three motion types are obviously different. The three motion types may be a hip adduction, a side-leg lift and a knee lift. To effectively recognize similar physical exercises, a motion recognition device may recognize the three motion types, and is additionally applied to recognize other motion types.

In addition, a physical exercise coach (or a senior physical exerciser) and a physical exercise beginner respectively do a first physical exercise and a second physical exercise compared to the first physical exercise. Because the physical exercise coach has received more training over a longer period, the first physical exercise is typically a predetermined standard exercise. Because the physical exercise beginner may have received less training over a shorter period, a deviation between the second physical exercise and the predetermined standard exercise is relatively large. This deviation is because a motion gesture of the second physical exercise deviates from that of the predetermined standard exercise, or because the second physical exercise is incomplete, or because the training received by the physical exercise beginner is insufficient, so that the second physical exercise may include an inadvertent or inefficient habitual motion to form the deviation. The inadvertent or inefficient habitual motion may be detected by means of the motion-sensing device, and thus the motion-sensing device reminds the physical exercise beginner to improve the second physical exercise, promotes the physical exercise beginner to do the predetermined standard exercise, and improves the outcome of the training operations.

It is appropriate that the motion-sensing device detects detailed variations in the motion during a physical exercise. For instance, a physical exerciser does a physical exercise of a skull crusher by means of a bench. The skull crusher includes movements of: moving the lower arm to an upper position above the eyes; and rotating the lower arm from horizontal to vertical. When the physical exerciser wants to more effectively exercise the muscles, the skull crusher may be adjusted to include more difficult movements of: moving the lower arm to a position at which the lower arm is almost perpendicular to the main body; and raising the lower arm to align with the upper arm. It is appropriate that the motion-sensing device recognizes the fine variations in the physical exercise, report the recognized motion type to the physical exerciser, and informs the physical exerciser when the physical exercise is finished and/or the relevant muscles have been exercised.

The physical exerciser may use a gymnastic apparatus in a gym to do the physical exercise. For instance, when the physical exerciser operates a seated row machine being a gymnastic apparatus and the two hands of the physical exerciser grasp a cross bar of the seated row machine to do the physical exercise, the motion-sensing device fastened to a body portion of the physical exerciser may recognize the physical exercise, wherein the two hands have a distance therebetween on the cross bar, and the distance is relatively narrower or wider to allow the exercised muscle group to change. For instance, when the physical exerciser does a sit-up exercise on a reclining seat in a gym, the motion-sensing device fastened to a body portion of the physical exerciser may recognize the sit-up exercise according to an external condition of the reclining seat. For instance, reclining seats in the gym have different inclination angles, and each of the physical exercisers may prefer a different inclination angle of a reclining seat, which varies from person to person. Under the external condition of the reclining seat, the motion-sensing device may obtain appropriate signals to analyze, and may accurately recognize the motion state, count the motion cycles and obtain the analysis results.

The conventional wearable motion-sensing device has a function confinement over a long period of time; and there is a demand to adapt to multiple conditions of a physical exercise and to recognize a result of the physical exercise. It is an objective of the present disclosure to provide a motion recognition device, which senses various body motions, recognize their motion types, count motion cycles of a body motion to obtain a motion cycle number, and store the motion cycle number, or a motion status or results of the body motion in a database, so that the motion data stored in the database may subsequently be processed and reused to provide a reference motion suggestion to the user of the motion recognition device. The motion recognition device is wearable and is especially suitable to the exerciser doing a physical exercise in a gym.

It is therefore an embodiment of the present disclosure to provide a motion recognition device. The motion recognition device includes a sensing unit and a processing unit. The sensing unit generates a sense signal in response to a body motion occurring at a specific position on a user's body, wherein the sense signal includes a first sense signal portion and a second sense signal portion different from the first sense signal portion, and the body motion belongs to a motion segment of a motion type. The processing unit processes the sense signal to generate a motion parameter signal structure including a fusion signal of the first and the second sense signal portions, and recognizes the specific position to determine an effective reference signal for recognition of the motion type based on the motion parameter signal structure.

It is another embodiment of the present disclosure to provide a motion recognition device. The motion recognition device includes a signal generating unit and a processing unit. The signal generating unit generates a motion parameter signal structure in response to a body motion occurring at a specific position on a user's body, wherein the body motion belongs to a motion type. The processing unit recognizes the specific position to determine an effective reference signal for recognition of the motion type based on the motion parameter signal structure.

It is still another embodiment of the present disclosure to provide a motion recognition method. The motion recognition method includes the following steps. A motion parameter signal structure is generated in response to a body motion occurring at a specific position on a user's body, wherein the body motion belongs to a motion type. Based on the motion parameter signal structure, the specific position is recognized to determine an effective reference signal for recognition of the motion type.

It is still another embodiment of the present disclosure to provide a motion recognition device. The motion recognition device includes a memory module and a processing module. The memory module stores a characteristic function code data unit associated with a first recognition value domain and a second recognition value domain adjacent to the first recognition value domain, wherein the first and the second recognition value domains respectively indicate a first motion type and a second motion type. The processing module obtains a specific motion characteristic value data unit from a specific motion sense signal, performs a calculation to generate a recognition value based on the characteristic function code data unit and the specific motion characteristic value data unit, and decides whether the recognition value belongs to one of the first and the second recognition value domains.

BRIEF DESCRIPTION OF THE DRAWINGS

The foregoing and other features and advantages of the present disclosure will be more clearly understood through the following descriptions with reference to the drawings, wherein.

DETAILED DESCRIPTION OF THE PREFERRED EMBODIMENTS

The present disclosure will now be described more specifically with reference to the following embodiments. It is to be noted that the following descriptions of preferred embodiments of this disclosure are presented herein for the purposes of illustration and description only; they are not intended to be exhaustive or to be limited to the precise form disclosed.

Figure 1:
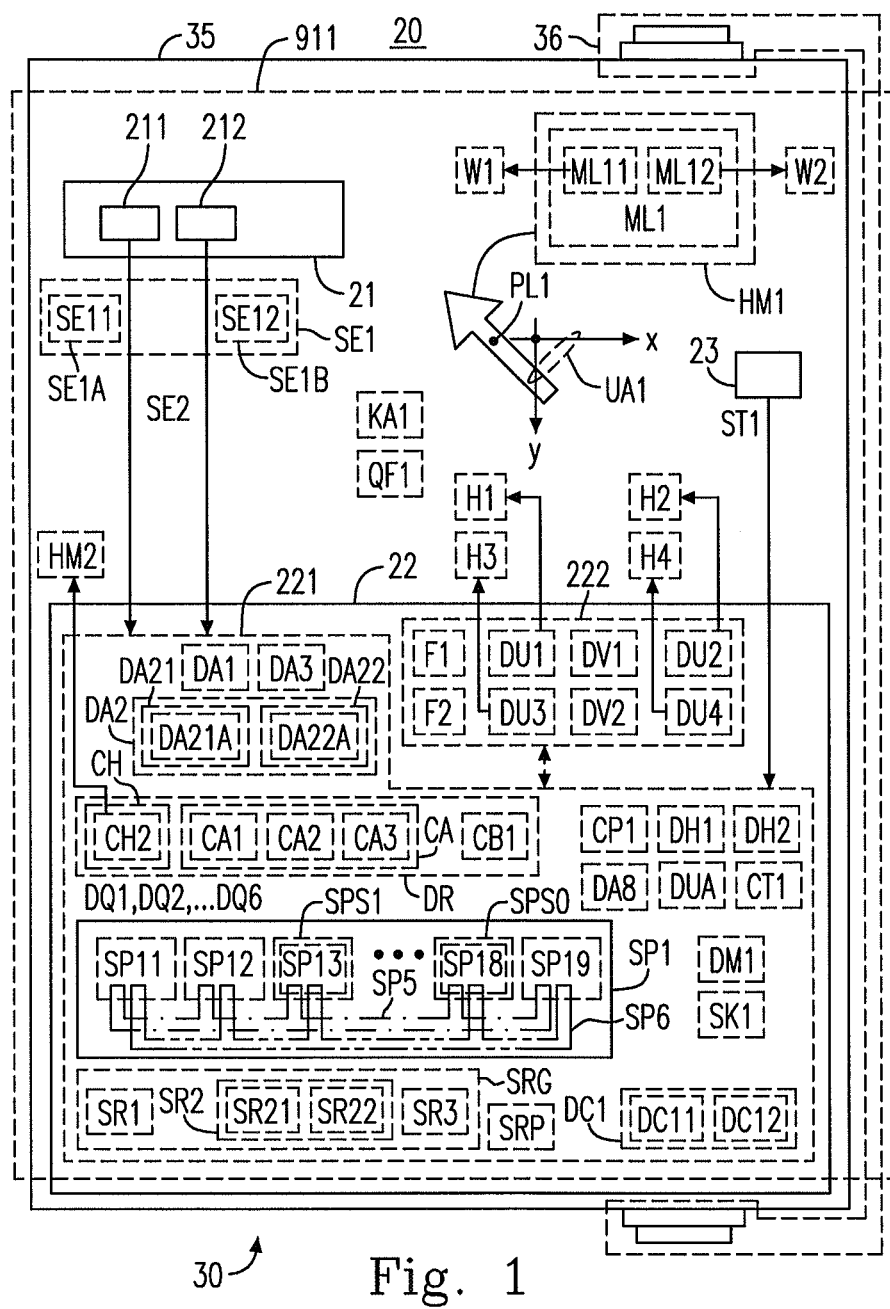
FIG. 1 is a schematic diagram showing a motion recognition device according to various embodiments of the present disclosure.
Figure 2:
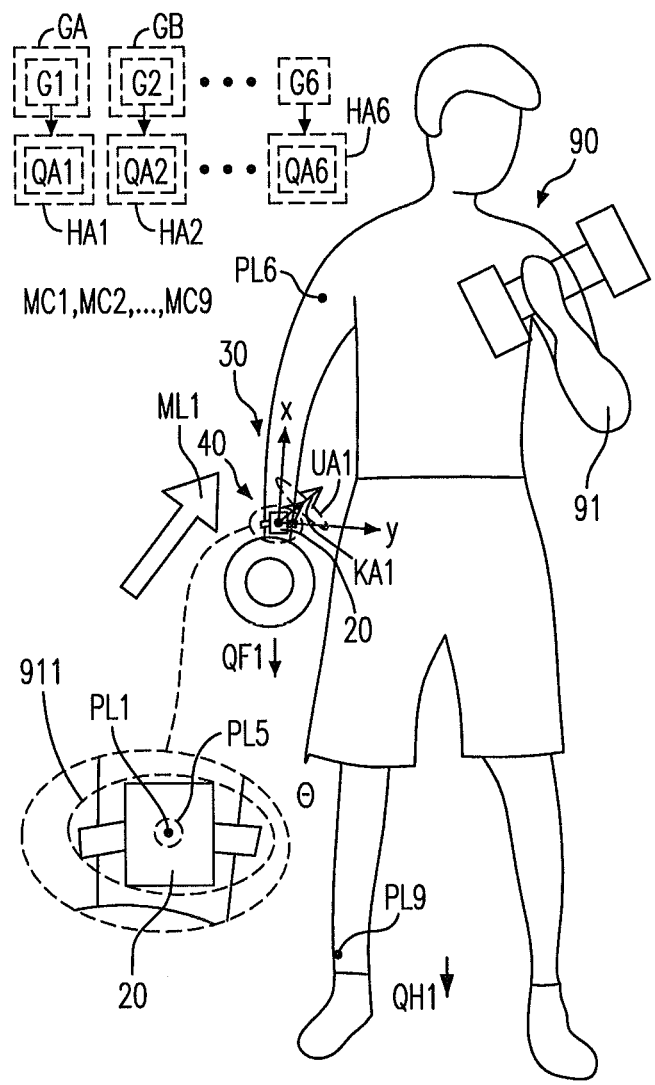
FIG. 2 is a schematic diagram showing a user wearing the motion recognition device illustrated in FIG. 1.

Please refer to FIG. 1 and FIG. 2. FIG. 1 is a schematic diagram showing a motion recognition device 20 according to various embodiments of the present disclosure. FIG. 2 is a schematic diagram showing a user 90 wearing the motion recognition device 20 illustrated in FIG. 1. As shown in FIGS. 1 and 2, the motion recognition device 20 includes a sensing unit 21 and a processing unit 22. The sensing unit 21 generates a sense signal SE1 in response to a first body motion ML1 occurring at a specific position PL1 on a user's body 91, wherein the sense signal SE1 includes a first sense signal portion SE1A and a second sense signal portion SE1B different from the first sense signal portion SE1A, and the first body motion ML1 belongs to a motion segment of a first motion type HM1. The processing unit 22 processes the sense signal SE1 to generate a motion parameter signal structure SP1 including a fusion signal SPS0 of the first and the second sense signal portions SE1A and SE1B, and recognizes the specific position PL1 to determine an effective reference signal SRP for recognition of the first motion type HM1 based on the motion parameter signal structure SP1.

The motion recognition device 20 is configured to have an orientation KA1, a gravity direction QF1 and a body coordinate system UA1 used to determine the orientation KA1, and is fastened at the specific position PL1. In some embodiments, the motion recognition device 20 has the user 90, which has the user's body 91 doing the first body motion ML1; and the user's body 91 has a plurality of different positions PL5, PL6, . . . PL9. The specific position PL1 is optionally selected from the plurality of different positions PL5, PL6, . . . PL9 on the user's body 91. The processing unit 22 is coupled to the sensing unit 21. The first motion type HM1 is one selected from a plurality of motion types HA1, HA2, . . . HA6. The plurality of motion types HA1, HA2, . . . HA6 are predetermined in relation to the specific position PL1, and respectively have a plurality of principal motion axis directions QA1, QA2, . . . QA6 in relation to the body coordinate system UA1. The plurality of principal motion axis directions QA1, QA2, . . . QA6 are detected beforehand to generate a plurality of principal motion axis direction data units DQ1, DQ2, . . . DQ6 respectively corresponding to the plurality of principal motion axis directions QA1, QA2, . . . QA6. For instance, the first body motion ML1 is a physical exercise; the first motion type HM1 is an exercise type; and the principal motion axis direction QA1 is a principal rotation axis direction or a principal translation axis direction.

The sense signal SE1 is generated in relation to the body coordinate system UA1, and includes an accelerometer signal SE11 and a gyroscope signal SE12, which are the first and the second sense signal portions SE1A and SE1B, respectively. For instance, the fusion signal SPS0 is generated by using a signal fusion operation. In a state that the orientation KA1 is directed to a predetermined direction QH1 in relation to the gravity direction QF1, the processing unit 22 generates a specific position code CP1 representing the specific position PL1 based on the motion parameter signal structure SP1, and thereby recognizes the specific position PL1. The predetermined direction QH1 is predetermined based on the specific position PL1. The predetermined direction QH1 and the gravity direction QF1 have a first angle θ therebetween. The fusion signal SPS0 is a signal of an estimated angle SK1 associated with the first angle θ. In this state, the processing unit 22 makes a first decision on whether the processing unit 22 detects a trigger signal ST1. When the first decision is positive, the processing unit 22 generates the specific position code CP1 based on the estimated angle SK1. For instance, the plurality of different positions PL5, PL6, . . . PL9 includes a wrist position, an upper arm position and an ankle position. For instance, the specific position PL1 is the wrist position, the upper arm position or the ankle position.

The processing unit 22 obtains a recognition reference data unit DR based on the specific position code CP1. The recognition reference data unit DR is predetermined based on the plurality of principal motion axis direction data units DQ1, DQ2, . . . DQ6, and includes a candidate reference signal code data unit CA and a motion type indicator data unit CH. The candidate reference signal code data unit CA includes a first candidate reference signal code CA2. The first candidate reference signal code CA2 represents a first candidate reference signal SR2 derived from the motion parameter signal structure SP1. The motion type indicator data unit CH includes a motion type indicator CH2 corresponding to the first candidate reference signal code CA2. The motion type indicator CH2 indicates one of an invalid motion type and a second motion type HM2 included in the plurality of motion types HA1, HA2, . . . HA6. The processing unit 22 determines the first candidate reference signal SR2 based on the motion parameter signal structure SP1 and the first candidate reference signal code CA2.

In some embodiments, the sensing unit 21 includes an accelerometer 211 and a gyroscope 212. Each of the accelerometer 211 and the gyroscope 212 is coupled to the processing unit 22. The accelerometer 211 generates the accelerometer signal SE11. The gyroscope 212 generates the gyroscope signal SE12. The sense signal SE1 includes the accelerometer signal SE11 and the gyroscope signal SE12. The processing unit 22 processes the accelerometer signal SE11 and the gyroscope signal SE12 to generate the motion parameter signal structure SP1 by performing the signal fusion operation. The signal fusion operation includes calculating the signal of the estimated angle SK1 based on the accelerometer signal SE11 and the gyroscope signal SE12.

In some embodiments, the motion recognition device 20 further includes a push button 23 coupled to the processing unit 22. The user's body 91 has a specific body portion 911 at the specific position PL1. The motion recognition device 20 is fastened to the specific body portion 911. The specific body portion 911 does the first body motion ML1 to drive the motion recognition device 20. In the state that the orientation KA1 is directed to the predetermined direction QH1 in relation to the gravity direction QF1, the push button 23 provides the trigger signal ST1 in response to a user button-press from the user 90. For instance, the orientation KA1 has a pointing reference axis; the user's body 91 is configured to have a reference position, and is configured to have a first predetermined limited outside area based on the reference position and an ergonomic principle, wherein the first predetermined limited outside area corresponds to the specific position PL1; and in this state, the pointing reference axis points to a first position in the first predetermined limited outside area. For instance, the user's body 91 is configured to have a plurality of predetermined limited outside areas based on the reference position and the ergonomic principle, wherein the plurality of predetermined limited outside areas are different, and respectively correspond to the plurality of different positions PL5, PL6, . . . PL9. For instance, the specific body portion 911 is a wrist, an upper arm or an ankle of the user's body 91.

In some embodiments, the first body motion ML1 includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. The motion parameter signal structure SP1 includes a first motion parameter signal structure portion SP5 and a second motion parameter signal structure portion SP6 respectively corresponding to the first and the second motion portions ML11 and ML12. The first candidate reference signal SR2 includes a first candidate reference signal portion SR21 and a second candidate reference signal portion SR22 respectively corresponding to the first and the second motion portions ML11 and ML12, wherein the second candidate reference signal portion SR22 is adjacent to the first candidate reference signal portion SR21. The processing unit 22 obtains a first motion characteristic value data unit DA2 from the motion parameter signal structure SP1 based on the first candidate reference signal SR2. For instance, the first and the second motion parameter signal structure portion SP5 and SP6 are respectively generated on the first and the second cycles. The first and the second candidate reference signal portion SR21 and SR22 are respectively generated on the first and the second cycles.

For instance, the first motion characteristic value data unit DA2 includes a first motion characteristic value data unit portion DA21 and a second motion characteristic value data unit portion DA22 respectively corresponding to the first and the second motion portions ML11 and ML12. The processing unit 22 obtains the first motion characteristic value data unit portion DA21 from the first motion parameter signal structure portion SP5 based on the first candidate reference signal portion SR21. The processing unit 22 obtains the second motion characteristic value data unit portion DA22 from the second motion parameter signal structure portion SP6 based on the second candidate reference signal portion SR22.

In some embodiments, the processing unit 22 generates a difference data unit DC1 based on the first and the second motion characteristic value data unit portions DA21 and DA22, and makes a second decision on whether the difference data unit DC1 satisfies a first specific condition for a periodic-motion start decision. When the second decision is positive, the processing unit 22 recognizes the effective reference signal SRP as the first candidate reference signal SR2, determines that the first body motion ML1 satisfies a predetermined periodic-motion start condition, and based on the motion type indicator CH2, makes a third decision on whether the motion type indicator CH2 indicates one selected from the plurality of motion types HA1, HA2, . . . HA6. When the third decision is positive, the processing unit 22, based on the motion type indicator CH2, recognizes the first motion type HM1 as the second motion type HM2, and obtains a motion type code CT1 representing the first motion type HM1.

The motion parameter signal structure SP1 includes a plurality of motion parameter signals SP11, SP12, SP13, . . . SP18 and SP19. The recognition reference data unit DR further includes a representative signal code CB1 representing a representative signal SPS1 included in the plurality of motion parameter signals SP11, SP12, SP13, . . . SP18 and SP19. The processing unit 22 determines the representative signal SPS1 based on the motion parameter signal structure SP1 and the representative signal code CB1. The processing unit 22 obtains a representative extreme value deviation DC11 between the first and the second motion characteristic value data unit portions DA21 and DA22 by comparing the first motion characteristic value data unit portion DA21 with the second motion characteristic value data unit portion DA22. For instance, the fusion signal SPS0 is the motion parameter signal SP18.

For instance, the first motion characteristic value data unit portion DA21 includes a first motion characteristic value data unit sub-portion DA21A corresponding to the representative signal SPS1, wherein the first motion characteristic value data unit sub-portion DA21A has a first maximum value, a first minimum value, and a first difference between the first maximum value and the first minimum value. The second motion characteristic value data unit portion DA22 includes a second motion characteristic value data unit sub-portion DA22A corresponding to the representative signal SPS1, wherein the second motion characteristic value data unit sub-portion DA22A has a second maximum value, a second minimum value, and a second difference between the second maximum value and the second minimum value. The processing unit 22 obtains a representative value difference DC12 from the first and the second differences. The difference data unit DC1 includes the representative extreme value deviation DC11 and the representative value difference DC12. The first specific condition includes a first sub-condition and a second sub-condition. The first sub-condition is that the representative extreme value deviation DC11 falls within a first predetermined value range. The second sub-condition is that the representative value difference DC12 falls within a second predetermined value range.

In some embodiments, the candidate reference signal code data unit CA further includes at least a second candidate reference signal code CA1 (and optionally a third candidate reference signal code CA3) representing at least a second candidate reference signal SR1 (and optionally a third candidate reference signal SR3). The second candidate reference signal code CA1 represents the second candidate reference signal SR1 derived from the motion parameter signal structure SP1. The first candidate reference signal SR1 and the at least a second candidate reference signal SR1 (and optionally SR3) constitute a candidate reference signal combination SRG.

The processing unit 22 determines the at least a second candidate reference signal SR1 (and optionally SR3) based on the motion parameter signal structure SP1 and the at least a second candidate reference signal code CA1 (and optionally CA3), and obtains at least a second motion characteristic value data unit DA1 (and optionally a third motion characteristic value data unit DA3) from the motion parameter signal structure SP1 based on the at least a second candidate reference signal SR1 (and optionally SR3). The at least a second motion characteristic value data unit DA1 (and optionally DA3) corresponds to the at least a second candidate reference signal SR1 (and optionally SR3). When the processing unit 22 processes the first motion characteristic value data unit DA2, the processing unit 22 processes the at least a second motion characteristic value data unit DA1 (and optionally DA3) to decide whether the candidate reference signal combination SRG includes the effective reference signal SRP.

In some embodiments, when the second decision is negative, the first body motion ML1 further has a third motion portion and a fourth motion portion adjacent to the third motion portion, and the processing unit 22 determines a fourth candidate reference signal anew based on the motion parameter signal structure SP1 and the candidate reference signal code data unit CA, obtains a fourth motion characteristic value data unit from the motion parameter signal structure SP1 based on the fourth candidate reference signal, and thereby decides whether the effective reference signal SRP is recognized as the fourth candidate reference signal. In some embodiments, when a decision on whether the candidate reference signal combination SRG includes the effective reference signal SRP is negative, the first body motion ML1 further has a third motion portion and a fourth motion portion adjacent to the third motion portion, and the processing unit 22 determines an additional candidate reference signal combination anew based on the motion parameter signal structure SP1 and the candidate reference signal code data unit CA, and decides whether the additional candidate reference signal combination includes the effective reference signal SRP. In some embodiments, the third motion portion is the second motion cycle ML12.

In some embodiments, the second motion cycle ML12 is later than the first motion cycle ML11; the fourth motion cycle is later than the third motion cycle; and the second motion characteristic value data unit portion DA22 includes a plurality of specific motion characteristic values. The processing unit 22 provides beforehand a first characteristic function code data unit F1, which is associated with the first candidate reference signal code CA2 and a first plurality of recognition value domains DU1, DU2 and DV1. The first characteristic function code data unit F1 is employed to indicate one of the first plurality of recognition value domains DU1, DU2 and DV1. The first plurality of recognition value domains DU1, DU2 and DV1 include a first recognition value domain DU1, a second recognition value domain DU2 adjacent to the first recognition value domain DU1, and a first confidence value domain DV1 between the first and the second recognition value domains DU1 and DU2. For instance, the first confidence value domain DV1 is optional. The first and the second recognition value domains DU1 and DU2 respectively indicate a third motion type H1 and a fourth motion type H2. Each of the third and the fourth motion types H1 and H2 is included in the plurality of motion types HA1, HA2, . . . HA6. The motion recognition device 22 establishes the first characteristic function code data unit F1 beforehand by sensing a plurality of body motions MC1, MC2, . . . MC9 occurring at the specific position PL1, wherein the plurality of body motions MC1, MC2, . . . MC9 are divided into a plurality of motion groups G1, G2, . . . G6 respectively belonging to the plurality of motion types HAL HA2, . . . HA6. The first characteristic function code data unit F1 represents a motion type cut function employed to indicate the one of the first plurality of recognition value domains DU1, DU2 and DV1, and is expressed based on a relationship among the plurality of specific motion characteristic values. For instance, the processing unit 22 provides the first plurality of recognition value domains DU1, DU2 and DV1 beforehand.

When the third decision is negative, the processing unit 22 performs a first calculation to generate a first recognition value DH1 based on the first characteristic function code data unit F1 and the second motion characteristic value data unit portion DA22, and makes a fourth decision on whether the first recognition value DH1 belongs to one of the first and the second recognition value domains DU1 and DU2. When the fourth decision is positive, the processing unit 22 determines an effective recognition value domain DUA in the first and the second recognition value domains DU1 and DU2 that the first recognition value DH1 belongs to, recognizes the first motion type HM1 as an effective motion type indicated by the effective recognition value domain DUA, and obtains the motion type code CT1 corresponding to the effective recognition value domain DUA. The processing unit 22 generates a motion measurement information DM1 associated with the first body motion ML1 based on the motion type code CT1.

In some embodiments, the processing unit 22 further provides beforehand a second characteristic function code data unit F2, which is associated with the first candidate reference signal code CA2 and a second plurality of recognition value domains DU3, DU4 and DV2. The second characteristic function code data unit F2 is different from the first characteristic function code data unit F1, and is employed to indicate one of the second plurality of recognition value domains DU3, DU4 and DV2. The second plurality of recognition value domains DU3, DU4 and DV2 include a third recognition value domain DU3, a fourth recognition value domain DU4 adjacent to the third recognition value domain DU3, and a second confidence value domain DV2 between the third and the fourth recognition value domains DU3 and DU4. For instance, the first confidence value domain DV1 is optional. The third and the fourth recognition value domains DU3 and DU4 respectively indicate a fifth motion type H3 and a sixth motion type H4. Each of the fifth and the sixth motion types H3 and H4 is included in the plurality of motion types HA1, HA2, . . . HA6. For instance, the processing unit 22 provides the second plurality of recognition value domains DU3, DU4 and DV2 beforehand.

In a second specific condition, one of the third and the fourth recognition value domains DU3 and DU4 at least partially overlaps with one of the first and the second recognition value domains DU1 and DU2. When the fourth decision is negative, the processing unit 22 performs a second calculation to generate a second recognition value DH2 based on the second characteristic function code data unit F2 and the second motion characteristic value data unit portion DA22, decides whether the second recognition value DH2 belongs to one of the third and the fourth recognition value domains DU3 and DU4, and thereby recognizes the first motion type HM1.

In various embodiments provided according to the illustrations in FIGS. 1 and 2, a motion recognition device 30 includes a memory module 222 and a processing module 221. The memory module 222 stores a first characteristic function code data unit F1 associated with a first recognition value domain DU1 and a second recognition value domain DU2 adjacent to the first recognition value domain DU1, wherein the first and the second recognition value domains DU1 and DU2 respectively indicate a first motion type H1 and a second motion type H2. The processing module 221 obtains a specific motion characteristic value data unit DA8 from a specific motion sense signal SE2, performs a first calculation to generate a first recognition value DH1 based on the first characteristic function code data unit F1 and the specific motion characteristic value data unit DA8, and decides whether the first recognition value DH1 belongs to one of the first and the second recognition value domains DU1 and DU2.

The motion recognition device 30 further includes a sensing unit 21. The sensing unit 21 generates the specific motion sense signal SE2 in response to a first body motion ML1 occurring at a specific position PL1 on a user's body 91, wherein the first body motion ML1 belongs to a motion segment of a third motion type HM1. For instance, the specific motion sense signal SE2 is the sense signal SE1. The memory module 222 and the processing module 221 are disposed in a processing unit 22 disposed in the motion recognition device 30. The processing module 221 is coupled to the memory module 222 and the sensing unit 21, processes the specific motion sense signal SE2 to generate a motion parameter signal structure SP1, and recognizes the specific position PL1 to determine an effective reference signal SRP for recognition of the third motion type HM1 based on the motion parameter signal structure SP1. The specific motion sense signal SE2 includes an accelerometer signal SE11 and a gyroscope signal SE12. The motion parameter signal structure SP1 includes a fusion signal SPS0 of the accelerometer signal SE11 and the gyroscope signal SE12. For instance, the fusion signal SPS0 is generated by using a signal fusion operation.

The motion recognition device 30 is configured to have an orientation KA1, a gravity direction QF1 and a body coordinate system UA1 used to determine the orientation KA1, and is fastened at the specific position PL1. In some embodiments, the motion recognition device 30 has the user 90, which has the user's body 91 doing the first body motion ML1; and the user's body 91 has a plurality of different positions PL5, PL6, . . . PL9. The specific position PL1 is optionally selected from the plurality of different positions PL5, PL6, . . . PL9 on the user's body 91. The third motion type HM1 is one selected from a plurality of motion types HA1, HA2, . . . HA6. The plurality of motion types HA1, HA2, . . . HA6 are predetermined in relation to the specific position PL1, and respectively have a plurality of principal motion axis directions QA1, QA2, . . . QA6 in relation to the body coordinate system UA1. The plurality of principal motion axis directions QA1, QA2, . . . QA6 are detected beforehand to generate a plurality of principal motion axis direction data units DQ1, DQ2, . . . DQ6 respectively corresponding to the plurality of principal motion axis directions QA1, QA2, . . . QA6. For instance, the first body motion ML1 is a physical exercise; the third motion type HM1 is an exercise type; and the principal motion axis direction QA1 is a principal rotation axis direction or a principal translation axis direction.

The specific motion sense signal SE2 is generated in relation to the body coordinate system UA1. In a state that the orientation KA1 is directed to a predetermined direction QH1 in relation to the gravity direction QF1, the processing module 221 generates a specific position code CP1 representing the specific position PL1 based on the motion parameter signal structure SP1, and thereby recognizes the specific position PL1. The predetermined direction QH1 is predetermined based on the specific position PL1. The predetermined direction QH1 and the gravity direction QF1 have a first angle $\theta$ therebetween. The motion parameter signal structure SP1 includes a signal of an estimated angle SK1 associated with the first angle $\theta$. In this state, the processing module 221 makes a first decision on whether the processing module 221 detects a trigger signal ST1. When the first decision is positive, the processing module 221 generates the specific position code CP1 based on the estimated angle SK1. For instance, the plurality of different positions PL5, PL6, . . . PL9 includes a wrist position, an upper arm position and an ankle position. For instance, the specific position PL1 is the wrist position, the upper arm position or the ankle position.

The processing module 221 obtains a recognition reference data unit DR based on the specific position code CP1. The recognition reference data unit DR is predetermined based on the plurality of principal motion axis direction data units DQ1, DQ2, . . . DQ6, is obtained from the memory module 222, and includes a candidate reference signal code data unit CA and a motion type indicator data unit CH. The candidate reference signal code data unit CA includes a first candidate reference signal code CA2. The first candidate reference signal code CA2 represents a first candidate reference signal SR2 derived from the motion parameter signal structure SP1. The motion type indicator data unit CH includes a motion type indicator CH2 corresponding to the first candidate reference signal code CA2. The motion type indicator CH2 indicates one of an invalid motion type and a fourth motion type HM2 included in the plurality of motion types HA1, HA2, . . . HA6. The processing module 221 determines the first candidate reference signal SR2 based on the motion parameter signal structure SP1 and the first candidate reference signal code CA2.

The processing module 221 determines the first candidate reference signal SR2 based on the motion parameter signal structure SP1 and the first candidate reference signal code CA2. The motion recognition device 30 establishes the first characteristic function code data unit F1 beforehand by sensing a plurality of body motions MC1, MC2, . . . MC9 occurring at the specific position PL1, wherein the plurality of body motions MC1, MC2, . . . MC9 are divided into a plurality of motion groups G1, G2, . . . G6 respectively belonging to the plurality of motion types HA1, HA2, . . . HA6, and the plurality of motion types HA1, HA2, . . . HA6 includes the first and the second motion types H1 and H2. The first characteristic function code data unit F1 represents a motion type cut function, and is associated with the first candidate reference signal code SR2 and a first plurality of recognition value domains DU1, DU2 and DV1. The first characteristic function code data unit F1 is employed to indicate one of the first plurality of recognition value domains DU1, DU2 and DV1. The first plurality of recognition value domains DU1, DU2 and DV1 include a first recognition value domain DU1, a second recognition value domain DU2 adjacent to the first recognition value domain DU1, and a first confidence value domain DV1 between the first and the second recognition value domains DU1 and DU2. For instance, the first confidence value domain DV1 is optional.

In some embodiments, the sensing unit 21 includes an accelerometer 211 and a gyroscope 212. Each of the accelerometer 211 and the gyroscope 212 is coupled to the processing module 221. The accelerometer 211 generates the accelerometer signal SE11. The gyroscope 212 generates the gyroscope signal SE12. The sense signal SE1 includes the accelerometer signal SE11 and the gyroscope signal SE12. The processing module 221 processes the accelerometer signal SE11 and the gyroscope signal SE12 to generate the motion parameter signal structure SP1 by performing the signal fusion operation. The signal fusion operation includes calculating the signal of the estimated angle SK1 based on the accelerometer signal SE11 and the gyroscope signal SE12.

In some embodiments, the motion recognition device 30 further includes a push button 23 coupled to the processing module 221. The user's body 91 has a specific body portion 911 at the specific position PL1. The motion recognition device 30 is fastened to the specific body portion 911. The specific body portion 911 does the first body motion ML1 to drive the motion recognition device 30. In the state that the orientation KA1 is directed to the predetermined direction QH1 in relation to the gravity direction QF1, the push button 23 provides the trigger signal ST1 in response to a user button-press from the user 90. For instance, the orientation KA1 has a pointing reference axis; the user's body 91 is configured to have a reference position, and is configured to have a first predetermined limited outside area based on the reference position and an ergonomic principle, wherein the first predetermined limited outside area corresponds to the specific position PL1; and in this state, the pointing reference axis points to a first position in the first predetermined limited outside area. For instance, the user's body 91 is configured to have a plurality of predetermined limited outside areas based on the reference position and the ergonomic principle, wherein the plurality of predetermined limited outside areas are different, and respectively correspond to the plurality of different positions PL5, PL6, . . . PL9. For instance, the specific body portion 911 is a wrist, an upper arm or an ankle of the user's body 91.

In some embodiments, after the trigger signal ST1 is provided, the first body motion ML1 includes a first motion portion ML11 and a second motion portion ML12 adjacent to the first motion portion ML11. The first and the second motion portions ML1 and ML12 respectively form a first motion cycle W1 and a second motion cycle W2 adjacent to the first motion cycle W1. The motion parameter signal structure SP1 includes a first motion parameter signal structure portion SP5 and a second motion parameter signal structure portion SP6 respectively corresponding to the first and the second motion portions ML11 and ML12. The first candidate reference signal SR2 includes a first candidate reference signal portion SR21 and a second candidate reference signal portion SR22 respectively corresponding to the first and the second motion portions ML11 and ML12, wherein the second candidate reference signal portion SR22 is adjacent to the first candidate reference signal portion SR21. The processing module 221 obtains a first motion characteristic value data unit DA2 from the motion parameter signal structure SP1 based on the first candidate reference signal SR2.

For instance, the first motion characteristic value data unit DA2 includes a first motion characteristic value data unit portion DA21 and a second motion characteristic value data unit portion DA22 respectively corresponding to the first and the second motion portions ML11 and ML12. The processing module 221 obtains the first motion characteristic value data unit portion DA21 from the first motion parameter signal structure portion SP5 based on the first candidate reference signal portion SR21. The processing module 221 obtains the second motion characteristic value data unit portion DA22 from the second motion parameter signal structure portion SP6 based on the second candidate reference signal portion SR22.

In some embodiments, the processing module 221 generates a difference data unit DC1 based on the first and the second motion characteristic value data unit portions DA21 and DA22, and makes a second decision on whether the difference data unit DC1 satisfies a first specific condition for a periodic-motion start decision. When the second decision is positive, the processing module 221 recognizes the effective reference signal SRP as the first candidate reference signal SR2, determines that the first body motion ML1 satisfies a predetermined periodic-motion start condition, and based on the motion type indicator CH2, makes a third decision on whether the motion type indicator CH2 indicates one selected from the plurality of motion types HA1, HA2, . . . HA6. When the third decision is positive, the processing module 221, based on the motion type indicator CH2, recognizes the third motion type HM1 as the fourth motion type HM2 based on the motion type indicator CH2, and obtains a motion type code CT1 representing the third motion type HM1.

The motion parameter signal structure SP1 includes a plurality of motion parameter signals SP11, SP12, SP13, . . . SP18 and SP19. The recognition reference data unit DR further includes a representative signal code CB1 representing a representative signal SPS1 included in the plurality of motion parameter signals SP11, SP12, SP13, . . . SP18 and SP19. The processing module 221 determines the representative signal SPS1 based on the motion parameter signal structure SP1 and the representative signal code CB1. The processing module 221 obtains a representative extreme value deviation DC11 between the first and the second motion characteristic value data unit portions DA21 and DA22 by comparing the first motion characteristic value data unit portion DA21 with the second motion characteristic value data unit portion DA22. For instance, the fusion signal SPS0 is the motion parameter signal SP18.

For instance, the first motion characteristic value data unit portion DA21 includes a first motion characteristic value data unit sub-portion DA21A corresponding to the representative signal SPS1, wherein the first motion characteristic value data unit sub-portion DA21A has a first maximum value, a first minimum value, and a first difference between the first maximum value and the first minimum value. The second motion characteristic value data unit portion DA22 includes a second motion characteristic value data unit sub-portion DA22A corresponding to the representative signal SPS1, wherein the second motion characteristic value data unit sub-portion DA22A has a second maximum value, a second minimum value, and a second difference between the second maximum value and the second minimum value. The processing module 221 obtains a representative value difference DC12 from the first and the second differences. The difference data unit DC1 includes the representative extreme value deviation DC11 and the representative value difference DC12. The first specific condition includes a first sub-condition and a second sub-condition. The first sub-condition is that the representative extreme value deviation DC11 falls within a first predetermined value range. The second sub-condition is that the representative value difference DC12 falls within a second predetermined value range.

In some embodiments, the candidate reference signal code data unit CA further includes at least a second candidate reference signal code CA1 (and optionally a third candidate reference signal code CA3) representing at least a second candidate reference signal SR1 (and optionally a third candidate reference signal SR3). The second candidate reference signal code CA1 represents the second candidate reference signal SR1 derived from the motion parameter signal structure SP1. The first candidate reference signal SR1 and the at least a second candidate reference signal SR1 (and optionally SR3) constitute a candidate reference signal combination SRG.

The processing module 221 determines the at least a second candidate reference signal SR1 (and optionally SR3) based on the motion parameter signal structure SP1 and the at least a second candidate reference signal code CA1 (and optionally CA3), and obtains at least a second motion characteristic value data unit DA1 (and optionally a third motion characteristic value data unit DA3) from the motion parameter signal structure SP1 based on the at least a second candidate reference signal SR1 (and optionally SR3). The at least a second motion characteristic value data unit DA1 (and optionally DA3) corresponds to the at least a second candidate reference signal SR1 (and optionally SR3). When the processing module 221 processes the first motion characteristic value data unit DA2, the processing module 221 processes the at least a second motion characteristic value data unit DA1 (and optionally DA3) to decide whether the candidate reference signal combination SRG includes the effective reference signal SRP.

In some embodiments, the second motion portion ML12 is later than the first motion portion ML11; and the second motion characteristic value data unit portion DA22 includes a plurality of specific motion characteristic values. For instance, the specific motion characteristic value data unit DA8 is the second motion characteristic value data unit portion DA22. The first characteristic function code data unit F1 represents the motion type cut function employed to indicate the one of the first plurality of recognition value domains DU1, DU2 and DV1; and the motion type cut function is expressed by a relationship among the plurality of specific motion characteristic values. When the third decision is negative, the processing module 221 performs the first calculation to generate the first recognition value DH1 based on the first characteristic function code data unit F1 and the second motion characteristic value data unit portion DA22, and makes a fourth decision on whether the first recognition value DH1 belongs to one of the first and the second recognition value domains DU1 and DU2. When the fourth decision is positive, the processing module 221 determines an effective recognition value domain DUA in the first and the second recognition value domains DU1 and DU2 that the first recognition value DH1 belongs to, recognizes the third motion type HM1 as an effective motion type indicated by the effective recognition value domain DUA, and obtains the motion type code CT1 corresponding to the effective recognition value domain DUA. The processing module 221 generates a motion measurement information DM1 associated with the first body motion ML1 based on the motion type code CT1.

In some embodiments, the memory module 222 further stores beforehand a second characteristic function code data unit F2, which is associated with the first candidate reference signal code CA2 and a second plurality of recognition value domains DU3, DU4 and DV2. The second characteristic function code data unit F2 is different from the first characteristic function code data unit F1, and is employed to indicate one of the second plurality of recognition value domains DU3, DU4 and DV2. The second plurality of recognition value domains DU3, DU4 and DV2 include a third recognition value domain DU3, a fourth recognition value domain DU4 adjacent to the third recognition value domain DU3, and a second confidence value domain DV2 between the third and the fourth recognition value domains DU3 and DU4. For instance, the first confidence value domain DV1 is optional. The third and the fourth recognition value domains DU3 and DU4 respectively indicate a fifth motion type H3 and a sixth motion type H4. Each of the fifth and the sixth motion types H3 and H4 is included in the plurality of motion types HA1, HA2, . . . HA6. For instance, the memory module 222 provides the first plurality of recognition value domains DU1, DU2 and DV1 and the second plurality of recognition value domains DU3, DU4 and DV2 beforehand.

In a second specific condition, one of the third and the fourth recognition value domains DU3 and DU4 at least partially overlaps with one of the first and the second recognition value domains DU1 and DU2. When the fourth decision is negative, the processing module 221 performs a second calculation to generate a second recognition value DH2 based on the second characteristic function code data unit F2 and the second motion characteristic value data unit portion DA22, decides whether the second recognition value DH2 belongs to one of the third and the fourth recognition value domains DU3 and DU4, and thereby recognizes the third motion type HM1.

Figure 3:
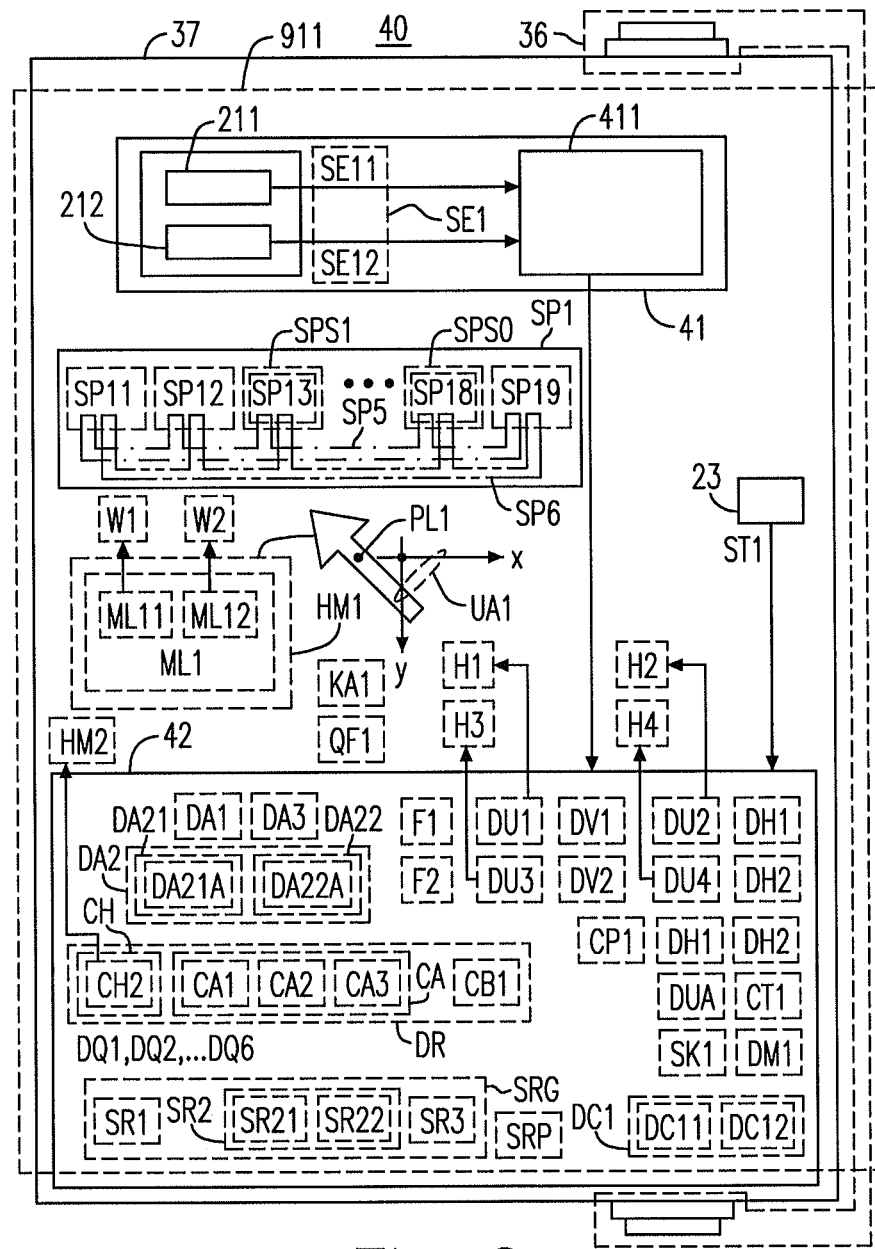
FIG. 3 is a schematic diagram showing a motion recognition device according to various embodiments of the present disclosure.

Please refer to FIG. 3, which is a schematic diagram showing a motion recognition device 40 according to various embodiments of the present disclosure. Please additionally refer to FIG. 2. As shown in FIGS. 2 and 3, the motion recognition device 40 includes a signal generating unit 41 and a processing unit 42. The signal generating unit 41 generates a motion parameter signal structure SP1 in response to a body motion ML1 occurring at a specific position PL1 on a user's body 91, wherein the body motion ML1 belongs to a first motion type HM1. The processing unit 42 recognizes the specific position PL1 to determine an effective reference signal SP1 for recognition of the first motion type HM1 based on the motion parameter signal structure SP1.

The motion recognition device 40 is configured to have an orientation KA1, a gravity direction QF1 and a body coordinate system UA1 used to determine the orientation KA1, and is fastened at the specific position PL1. The specific position PL1 is optionally selected from the plurality of different positions PL5, PL6, . . . PL9 on the user's body 91. In some embodiments, the signal generating unit 41 is coupled to the processing unit 42, and includes a sensing unit 21 and a converting unit 411 coupled to the sensing unit 21. The sensing unit 21 generates a sense signal SE1 in response to the body motion ML1, wherein the body motion ML1 belongs to a motion segment of the first motion type HM1. The converting unit 411 is coupled to the processing unit 42, and generates the motion parameter signal structure SP1 in response to the sense signal SE1.

In some embodiments, the sensing unit 21 includes an accelerometer 211 and a gyroscope 212. Each of the accelerometer 211 and the gyroscope 212 is coupled to the converting unit 411. The accelerometer 211 generates an accelerometer signal SE11. The gyroscope 212 generates a gyroscope signal SE12. The sense signal SE1 includes the accelerometer signal SE11 and the gyroscope signal SE12. The converting unit 411 processes the accelerometer signal SE11 and the gyroscope signal SE12 to generate the motion parameter signal structure SP1. The motion parameter signal structure SP1 includes a fusion signal SPS0 of the accelerometer signal SE11 and the gyroscope signal SE12. For instance, the fusion signal SPS0 is generated by using a signal fusion operation.

The first motion type HM1 is one selected from a plurality of motion types HA1, HA2, . . . HA6. The plurality of motion types HAL HA2, . . . HA6 are predetermined in relation to the specific position PL1, and respectively have a plurality of principal motion axis directions QA1, QA2, . . . QA6 in relation to the body coordinate system UA1. The plurality of principal motion axis directions QA1, QA2, . . . QA6 are detected beforehand to generate a plurality of principal motion axis direction data units DQ1, DQ2, . . . DQ6 respectively corresponding to the plurality of principal motion axis directions QA1, QA2, . . . QA6. The motion parameter signal structure SP1 is generated in relation to the body coordinate system UA1. In a state that the orientation KA1 is directed to a predetermined direction QH1 in relation to the gravity direction QF1, the processing unit 42 generates a specific position code CP1 representing the specific position PL1 based on the motion parameter signal structure SP1, and thereby recognizes the specific position PL1. The motion recognition device 40 further includes a push button 23 coupled to the processing unit 42. In the state that the orientation KA1 is directed to the predetermined direction QH1 in relation to the gravity direction QF1, the push button 23 provides the trigger signal ST1 in response to a user button-press from the user 90.

The processing unit 42 obtains a recognition reference data unit DR based on the specific position code CP1. The recognition reference data unit DR is predetermined based on the plurality of principal motion axis direction data units DQ1, DQ2, . . . DQ6, and includes a candidate reference signal code data unit CA and a motion type indicator data unit CH. The candidate reference signal code data unit CA includes a candidate reference signal code CA2. The candidate reference signal code CA2 represents a candidate reference signal SR2 derived from the motion parameter signal structure SP1. The motion type indicator data unit CH includes a motion type indicator CH2 corresponding to the candidate reference signal code CA2. The motion type indicator CH2 indicates one of an invalid motion type and a second motion type HM2 included in the plurality of motion types HAL HA2, . . . HA6. The processing unit 42 determines the candidate reference signal SR2 based on the motion parameter signal structure SP1 and the candidate reference signal code CA2.

In some embodiments, the body motion ML1 includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. The processing unit 42 obtains a motion characteristic value data unit DA2 from the motion parameter signal structure SP1 based on the candidate reference signal SR2. The motion characteristic value data unit DA2 includes a first motion characteristic value data unit portion DA21 and a second motion characteristic value data unit portion DA22 respectively corresponding to the first and the second motion portions ML11 and ML12. The processing unit 42 generates a difference data unit DC1 based on the first and the second motion characteristic value data unit portions DA21 and DA22. The processing unit 42 makes a first decision on whether the difference data unit DC1 satisfies a specific condition for a periodic-motion start decision. When the first decision is positive, the processing unit 42 recognizes the effective reference signal SRP as the candidate reference signal SR2, and based on the motion type indicator CH2, makes a second decision on whether the motion type indicator CH2 indicates one selected from the plurality of motion types HA1, HA2, . . . HA6. When the second decision is positive, the processing unit 42, based on the motion type indicator CH2, recognizes the first motion type HM1 as the second motion type HM2, and obtains a motion type code CT1 representing the first motion type HM1.

In some embodiments, the second motion portion ML12 is later than the first motion portion ML11. The processing unit 42 provides beforehand a characteristic function code data unit F1. The characteristic function code data unit F1 is associated with the candidate reference signal code CA2, a first recognition value domain DU1, and a second recognition value domain DU2 adjacent to the first recognition value domain DU1. The first and the second recognition value domains DU1 and DU2 respectively indicate a third motion type H1 and a fourth motion type H2. Each of the third and the fourth motion types H1 and H2 is included in the plurality of motion types HA1, HA2, . . . HA6. When the second decision is negative, the processing unit 42 performs a first calculation to generate a recognition value DH1 based on the first characteristic function code data unit F1 and the second motion characteristic value data unit portion DA22, determines an effective recognition value domain DUA in the first and the second recognition value domains DU1 and DU2 that the recognition value DH1 belongs to, recognizes the first motion type HM1 as an effective motion type indicated by the effective recognition value domain DUA, and obtains the motion type code CT1 corresponding to the effective recognition value domain DUA. For instance, the processing unit 42 provides the first recognition value domain DU1 and the second recognition value domain DU2 beforehand.

In various embodiments provided according to the illustrations in FIGS. 1, 2 and 3, a motion recognition method includes the following steps. A motion parameter signal structure SP1 is generated in response to a first body motion ML1 occurring at a specific position PL1 on a user's body 91, wherein the first body motion ML1 belongs to a first motion type HM1. The specific position PL1 is recognized to determine an effective reference signal SRP for recognition of the first motion type HM1 based on the motion parameter signal structure SP1.

The motion recognition method further includes a step: a motion recognition device 20, 30 or 40 is provided. The motion recognition device 20, 30 or 40 is configured to have an orientation KA1, a gravity direction QF1 and a body coordinate system UA1 used to determine the orientation KA1, and is fastened at the specific position PL1. The first body motion ML1 belongs to a motion segment of a first motion type HM1. The specific position PL1 is optionally selected from a plurality of different positions PL5, PL6, . . . PL9 on the user's body 91. The step of generating the motion parameter signal structure SP1 in response to the first body motion ML1 includes the following sub-steps: a sense signal SE1 associated with the body coordinate system UA1 is generated in response to the first body motion ML1, wherein the sense signal SE1 includes an accelerometer signal SE11 and a gyroscope signal SE12; and the sense signal SE1 is processed to generate the motion parameter signal structure SP1. The motion parameter signal structure SP1 includes a fusion signal SPS0 of the accelerometer signal SE11 and the gyroscope signal SE12. For instance, the fusion signal SPS0 is generated by using a signal fusion operation.

The first motion type HM1 is one selected from a plurality of motion types HA1, HA2, . . . HA6. The plurality of motion types HAL HA2, . . . HA6 are predetermined in relation to the specific position PL1, and respectively have a plurality of principal motion axis directions QA1, QA2, . . . QA6 in relation to the body coordinate system UA1. The plurality of principal motion axis directions QA1, QA2, . . . QA6 are detected beforehand to generate a plurality of principal motion axis direction data units DQ1, DQ2, . . . DQ6 respectively corresponding to the plurality of principal motion axis directions QA1, QA2, . . . QA6. For instance, the first body motion ML1 is a physical exercise; the first motion type HM1 is an exercise type; and the principal motion axis direction QA1 is a principal rotation axis direction or a principal translation axis direction. The motion recognition method further includes a step: in a state that the orientation KA1 is directed to a predetermined direction QH1 in relation to the gravity direction QF1, a specific position code CP1 representing the specific position PL1 is generated based on the motion parameter signal structure SP1, thereby recognizing the specific position PL1.

For instance, the predetermined direction QH1 is predetermined based on the specific position PL1. The predetermined direction QH1 and the gravity direction QF1 have a first angle θ therebetween. The fusion signal SPS0 is a signal of an estimated angle SK1 associated with the first angle θ. The step of generating the specific position code CP1 includes the following sub-steps: in this state, a first decision is made on whether a trigger signal ST1 is detected; in this state, a trigger signal ST1 is provided in response to a user button-press from the user 90; and when the first decision is positive, the specific position code CP1 is generated based on the estimated angle SK1.

The motion recognition method further includes a step: a recognition reference data unit DR is obtained based on the specific position code CP1. The recognition reference data unit DR is predetermined based on the plurality of principal motion axis direction data units DQ1, DQ2, . . . DQ6, and includes a candidate reference signal code data unit CA and a motion type indicator data unit CH. The candidate reference signal code data unit CA includes a first candidate reference signal code CA2. The first candidate reference signal code CA2 represents a first candidate reference signal SR2 derived from the motion parameter signal structure SP1. The motion type indicator data unit CH includes a motion type indicator CH2 corresponding to the first candidate reference signal code CA2. The motion type indicator CH2 indicates one of an invalid motion type and a second motion type HM2 included in the plurality of motion types HA1, HA2, . . . HA6. The motion recognition method further includes a step: the first candidate reference signal SR2 is determined based on the motion parameter signal structure SP1 and the first candidate reference signal code CA2.

The motion parameter signal structure SP1 includes a plurality of motion parameter signals SP11, SP12, SP13, . . . SP18 and SP19. After the trigger signal ST1 is provided, the first body motion ML1 includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. The motion parameter signal structure SP1 includes a first motion parameter signal structure portion SP5 and a second motion parameter signal structure portion SP6 respectively corresponding to the first and the second motion portions ML11 and ML12. The first candidate reference signal SR2 includes a first candidate reference signal portion SR21 and a second candidate reference signal portion SR22 respectively corresponding to the first and the second motion portions ML11 and ML12, wherein the second candidate reference signal portion SR22 is adjacent to the first candidate reference signal portion SR21. The recognition reference data unit DR further includes a representative signal code CB1 representing a representative signal SPS1 included in the plurality of motion parameter signals SP11, SP12, SP13, . . . SP18 and SP19. For instance, the fusion signal SPS0 is the motion parameter signal SP18.

In some embodiments, the motion recognition method further includes a step: a first motion characteristic value data unit DA2 is obtained from the motion parameter signal structure SP1 based on the first candidate reference signal SR2. The first motion characteristic value data unit DA2 includes a first motion characteristic value data unit portion DA21 and a second motion characteristic value data unit portion DA22 respectively corresponding to the first and the second motion portions ML11 and ML12. The step of obtaining the first motion characteristic value data unit DA2 includes the following sub-steps: the first motion characteristic value data unit portion DA21 is obtained from the first motion parameter signal structure portion SP5 based on the first candidate reference signal portion SR21; and the second motion characteristic value data unit portion DA22 is obtained from the second motion parameter signal structure portion SP6 based on the second candidate reference signal portion SR22.

In some embodiments, the motion recognition method further includes the following steps. A difference data unit DC1 is generated based on the first and the second motion characteristic value data unit portions DA21 and DA22. A second decision is made on whether the difference data unit DC1 satisfies a first specific condition for a periodic-motion start decision. When the second decision is positive, the effective reference signal SRP is recognized as the first candidate reference signal SR2, it is determined that the first body motion ML1 satisfies a predetermined periodic-motion start condition, and based on the motion type indicator CH2, a third decision is made on whether the motion type indicator CH2 indicates one selected from the plurality of motion types HA1, HA2, . . . HA6. When the third decision is positive, based on the motion type indicator CH2, the first motion type HM1 is recognized as the second motion type HM2, and a motion type code CT1 representing the first motion type HM1 is obtained.

The step of generating the difference data unit DC1 includes the following sub-steps: a representative extreme value deviation DC11 between the first and the second motion characteristic value data unit portions DA21 and DA22 is obtained by comparing the first motion characteristic value data unit portion DA21 with the second motion characteristic value data unit portion DA22; and the representative signal SPS1 is determined based on the motion parameter signal structure SP1 and the representative signal code CB1. For instance, the first motion characteristic value data unit portion DA21 includes a first motion characteristic value data unit sub-portion DA21A corresponding to the representative signal SPS1, wherein the first motion characteristic value data unit sub-portion DA21A has a first maximum value, a first minimum value, and a first difference between the first maximum value and the first minimum value. The second motion characteristic value data unit portion DA22 includes a second motion characteristic value data unit sub-portion DA22A corresponding to the representative signal SPS1, wherein the second motion characteristic value data unit sub-portion DA22A has a second maximum value, a second minimum value, and a second difference between the second maximum value and the second minimum value. The step of generating the difference data unit DC1 further includes a sub-step: a representative value difference DC12 is obtained from the first and the second differences, wherein the difference data unit DC1 includes the representative extreme value deviation DC11 and the representative value difference DC12.

In some embodiments, the first specific condition includes a first sub-condition and a second sub-condition. The first sub-condition is that the representative extreme value deviation DC11 falls within a first predetermined value range. The second sub-condition is that the representative value difference DC12 falls within a second predetermined value range. The candidate reference signal code data unit CA further includes at least a second candidate reference signal code CA1 (and optionally a third candidate reference signal code CA3) representing at least a second candidate reference signal SR1 (and optionally a third candidate reference signal SR3). The second candidate reference signal code CA1 represents the second candidate reference signal SR1 derived from the motion parameter signal structure SP1. The first candidate reference signal SR1 and the at least a second candidate reference signal SR1 (and optionally SR3) constitute a candidate reference signal combination SRG.

The motion recognition method further includes the following steps. The at least a second candidate reference signal SR1 (and optionally SR3) is determined based on the motion parameter signal structure SP1 and the at least a second candidate reference signal code CA1 (and optionally CA3). At least a second motion characteristic value data unit DA1 (and optionally a third motion characteristic value data unit DA3) is obtained from the motion parameter signal structure SP1 based on the at least a second candidate reference signal SR1 (and optionally SR3), wherein the at least a second motion characteristic value data unit DA1 (and optionally DA3) corresponds to the at least a second candidate reference signal SR1 (and optionally SR3). When the first motion characteristic value data unit DA2 is processed, the at least a second motion characteristic value data unit DA1 (and optionally DA3) is processed to decide whether the candidate reference signal combination SRG includes the effective reference signal SRP.

In some embodiments, the second motion portion ML12 is later than the first motion portion ML11; and the second motion characteristic value data unit portion DA22 includes a plurality of specific motion characteristic values. The motion recognition method further includes a step: a first characteristic function code data unit F1 is provided beforehand by sensing a plurality of body motions MC1, MC2, . . . MC9 occurring at the specific position PL1. The first characteristic function code data unit F1 is associated with the first candidate reference signal code CA2 and a first plurality of recognition value domains DU1, DU2 and DV1. The first characteristic function code data unit F1 is employed to indicate one of the first plurality of recognition value domains DU1, DU2 and DV1. The first plurality of recognition value domains DU1, DU2 and DV1 include a first recognition value domain DU1, a second recognition value domain DU2 adjacent to the first recognition value domain DU1, and a first confidence value domain DV1 between the first and the second recognition value domains DU1 and DU2. For instance, the first confidence value domain DV1 is optional. The first and the second recognition value domains DU1 and DU2 respectively indicate a third motion type H1 and a fourth motion type H2. Each of the third and the fourth motion types H1 and H2 is included in the plurality of motion types HA1, HA2, . . . HA6. The plurality of body motions MC1, MC2, . . . MC9 are divided into a plurality of motion groups G1, G2, . . . G6 respectively belonging to the plurality of motion types HAL HA2, . . . HA6. The first characteristic function code data unit F1 represents a motion type cut function employed to indicate the one of the first plurality of recognition value domains DU1, DU2 and DV1, and is expressed based on a relationship among the plurality of specific motion characteristic values.

The motion recognition method further includes the following steps. When the third decision is negative, a first calculation is performed to generate a first recognition value DH1 based on the first characteristic function code data unit F1 and the second motion characteristic value data unit portion DA22, and a fourth decision is made on whether the first recognition value DH1 belongs to one of the first and the second recognition value domains DU1 and DU2. When the fourth decision is positive, an effective recognition value domain DUA that the first recognition value DH1 belongs to is determined in the first and the second recognition value domains DU1 and DU2, the first motion type HM1 is recognized as an effective motion type indicated by the effective recognition value domain DUA, and the motion type code CT1 corresponding to the effective recognition value domain DUA is obtained. A motion measurement information DM1 associated with the first body motion ML1 is generated based on the motion type code CT1. A second characteristic function code data unit F2 is provided beforehand.

For instance, the second characteristic function code data unit F2 is associated with the first candidate reference signal code CA2 and a second plurality of recognition value domains DU3, DU4 and DV2. The second characteristic function code data unit F2 is different from the first characteristic function code data unit F1, and is employed to indicate one of the second plurality of recognition value domains DU3, DU4 and DV2. The second plurality of recognition value domains DU3, DU4 and DV2 include a third recognition value domain DU3, a fourth recognition value domain DU4 adjacent to the third recognition value domain DU3, and a second confidence value domain DV2 between the third and the fourth recognition value domains DU3 and DU4. For instance, the first confidence value domain DV1 is optional. The third and the fourth recognition value domains DU3 and DU4 respectively indicate a fifth motion type H3 and a sixth motion type H4. Each of the fifth and the sixth motion types H3 and H4 is included in the plurality of motion types HA1, HA2, . . . HA6.

In a second specific condition, one of the third and the fourth recognition value domains DU3 and DU4 at least partially overlaps with one of the first and the second recognition value domains DU1 and DU2. The motion recognition method further includes a step: when the fourth decision is negative, a second calculation is performed to generate a second recognition value DH2 based on the second characteristic function code data unit F2 and the second motion characteristic value data unit portions DA21 and DA22, and whether the second recognition value DH2 belongs to one of the third and the fourth recognition value domains DU3 and DU4 is decided, thereby recognizing the first motion type HM1.

In some embodiments, each of the motion recognition devices 20, 30 and 40 has a wearable motion-sensing device structure, a motion recognition operation means and a motion recognition algorithm, and employs the techniques including a user fastening means, a user operation means, a measurement means and a motion recognition means. Each of the motion recognition devices 20 and 30 includes an operating unit 35 and a coupling unit 36 coupled to the operating unit 35. The operating unit 35 includes the sensing unit 21 and the processing unit 22. The motion recognition device 40 includes an operating unit 37 and a coupling unit 36 coupled to the operating unit 37. The operating unit 37 includes the signal generating unit 41 and the processing unit 42, wherein the signal generating unit 41 includes the sensing unit 21. Any of the motion recognition devices 20, 30 and 40 may serve as a wearable device, is coupled to the specific body portion 911 of the user 90 by using the coupling unit 36. For instance, the coupling unit 36 is a fastening component. For instance, the coupling unit 36 is like a watch strap.

In some embodiments, the fastening component has at least two stable states, and the wearable device uses the fastening component to couple the wearable device to the specific body portion 911 on the user 90. The sensing unit 21 of the wearable device may be a motion-sensing module. The fastening component may have a deformation to form a stable state of spread and a stable state of crimp. When the specific body portion 911 doing the first body motion ML1 is at least partially surrounded by the fastening component, the fastening component deforms to form the stable state of crimp, and is fixed to the specific body portion 911. The fastening component has a stable property in the stable state of spread; and in the stable state of spread, the operating unit 35 or 37 is mounted to the fastening component.

Please refer to Table 1, which is a table showing various physical exercise types according to various embodiments of the present disclosure. In some embodiments, the wearable device is fastened at the specific position PL1, or is fastened to the specific body portion 911. The specific position PL1 may be selected from the plurality of different positions PL5, PL6, ... PL9 on the user's body 91. The plurality of different positions PL5, PL6, ... PL9 include the wrist position, the upper arm position and the ankle position. The wearable device is fastened to the specific body portion 911 with the fastening component, which is one selected from a plurality of body portions. The plurality of body portions include the wrist, the upper arm and the ankle, so that the wearable device may be used to sense the body motions (such as the physical exercises) associated with at least one selected from a group consisting of the palm, the forearm, the upper arm, the shoulder, the chest, the back, the waist, the buttock, the thigh, the knee, the shin, the foot, and so forth. The physical exercise types, which are examples of the body motion types, are shown in Table 1.

TABLE 1

Figure 4A:
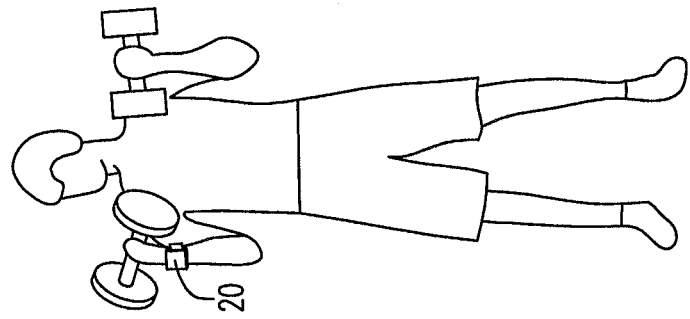
FIG. 4A, FIG. 4B and FIG. 4C are schematic diagrams showing a physical exercise type recognized by a motion recognition device fastened to a wrist.
Figure 4B:
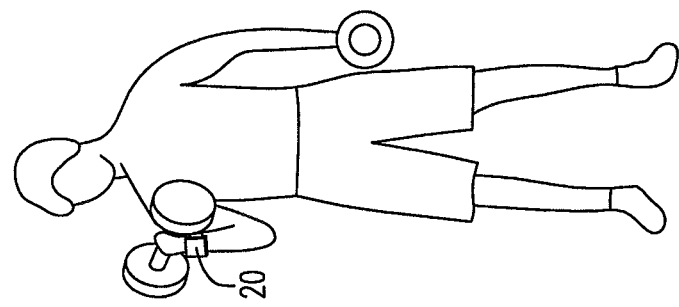
Figure 4C:
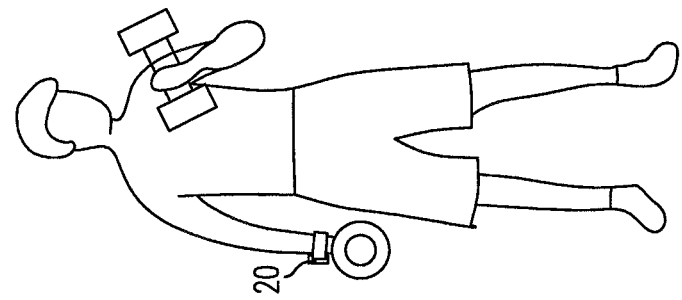
Figure 5:
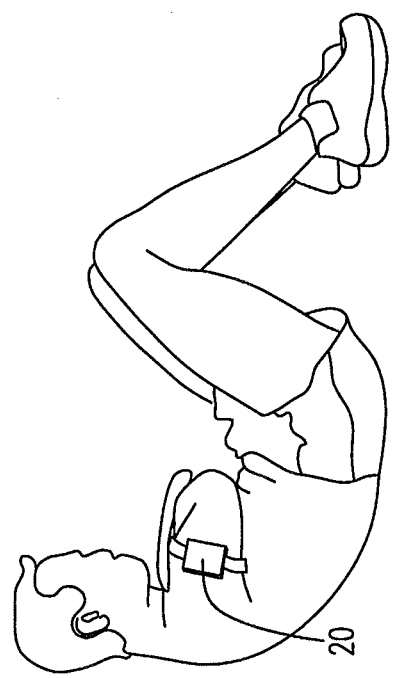
FIG. 5 is a schematic diagram showing a physical exercise type recognized by a motion recognition device fastened to an upper arm.
Figure 6:
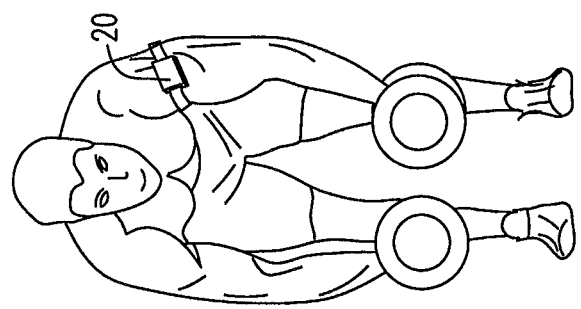
FIG. 6 is a schematic diagram showing a physical exercise type recognized by a motion recognition device fastened to an upper arm.
Figure 7A:
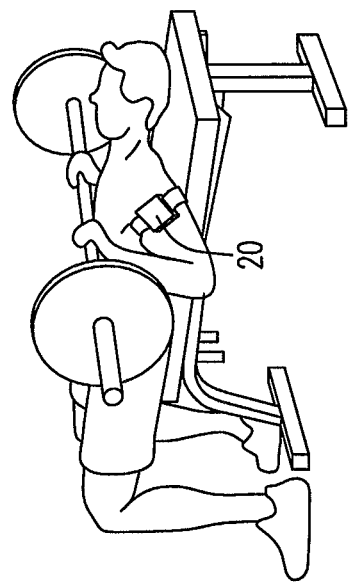
FIG. 7A and FIG. 7B are schematic diagrams showing a physical exercise type recognized by a motion recognition device fastened to an upper arm.
Figure 7B:
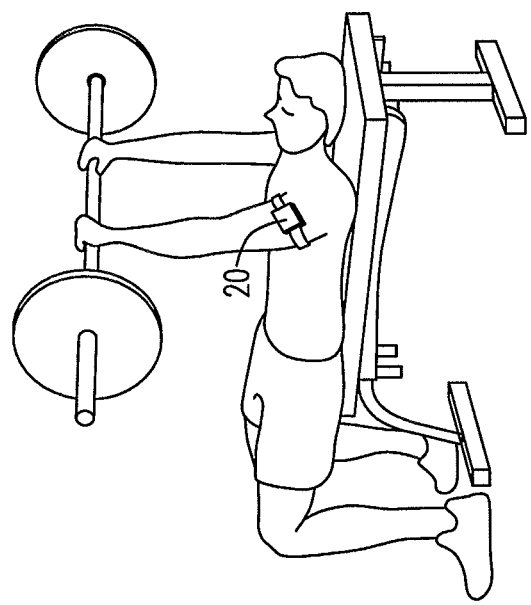
Figure 10B:
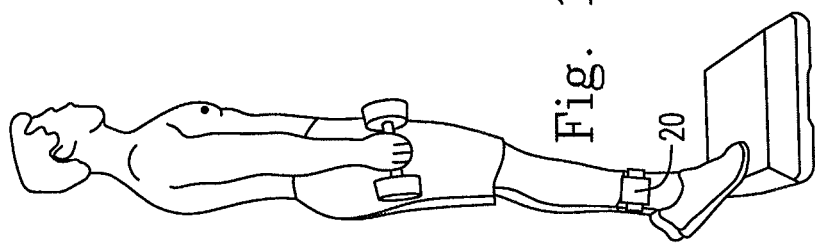
FIG. 10A and FIG. 10B are schematic diagrams showing a physical exercise type recognized by a motion recognition device fastened to an ankle.
Figure 10A:
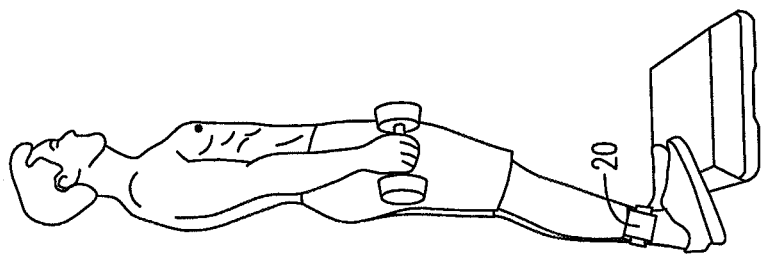
Figure 8:
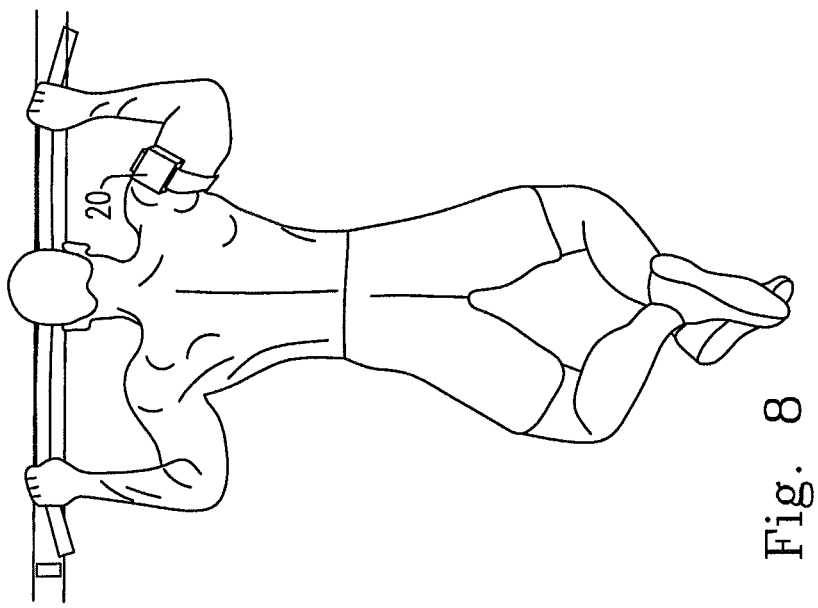
FIG. 8 is a schematic diagram showing a physical exercise type recognized by a motion recognition device fastened to an upper arm.
Figure 9B:
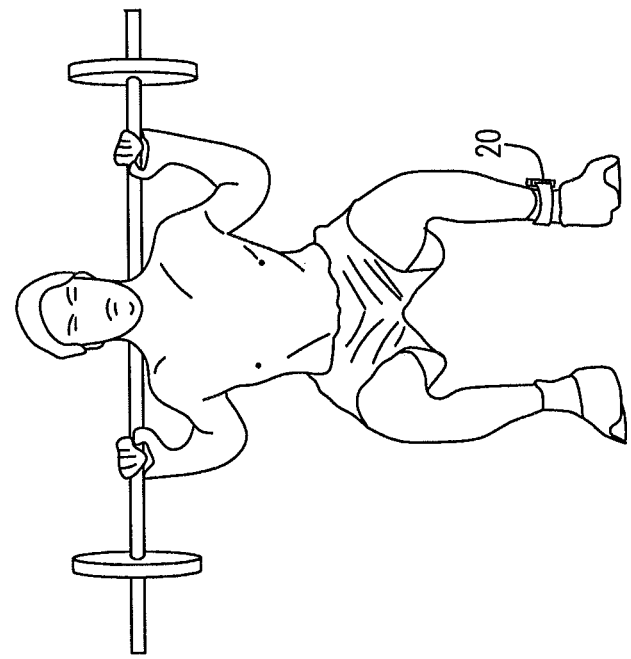
FIG. 9A and FIG. 9B are schematic diagrams showing a physical exercise type recognized by a motion recognition device fastened to an ankle.
Figure 9A:
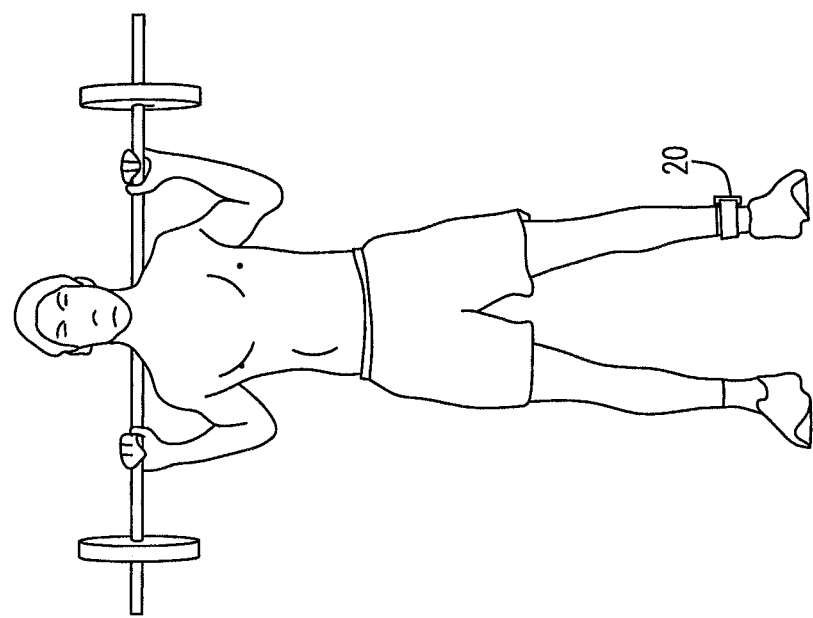

| Body Portion | Muscle | Physical Exercise Type | FIG. |
|---|---|---|---|
| Wrist | Triceps | Triceps Push-Down Supine Triceps Extension (Skull Crushers) Dumbbell Overhead Triceps Extension | FIG. 4A, FIG. 4B and FIG. 4C |
| Upper Arm | Biceps | Curls | |
| | Abdominals | Sit-Ups | |
| | Shoulder | Lateral-Raise Dumbbell Shoulder Press | FIG. 5 |
| | Chest | Bench Press Push-Up Butterfly | FIG. 6 |
| | Lats | Pull-Ups Pull-Down Abdominal Crunch | FIG. 7A and FIG. 7B |
| | Middle Back | Bent Over Row Seated Row | FIG. 8 |
| | Lower Back | Dead Lifts | |
| Ankle | Abductors | Hip Adduction Side Leg Raises | FIG. 9A and FIG. 9B |
| | Quadriceps | Squat | |
| | Abdominals | Vertical Leg Raises | FIG. 10A and |
| | Calves | Calf Raise | FIG. 10B |

In some embodiments, the user 90 generally does the physical exercise to exercise the body muscles by operating a gymnastic apparatus or a load, wherein the load includes a dumbbell, a barbell, or the like. The exercises most commonly performed include a wrist exercise, an upper arm exercise, a leg exercise, and so forth, and belongs to various physical exercise types as shown in Table 1. The user 90 does these exercises to exercise and strengthen the muscles in the body portions including the hand, the arm, the foot, the leg, the chest, the back, the shoulder, the waist, the buttocks, and so forth, and thus accomplish the objectives of health and body shaping. When the user 90 does the physical exercises occurring at the body portions including the arm, the leg, and so forth, the relevant wrist, upper arm or ankle has an obvious motion. Therefore, in order to precisely detect the operation of a physical exercise, comfortably wear the motion recognition device 20 at the specific body position, and consider the natural acceptability of the fastening comfort over a long period of time, the wrist position, the upper arm position, the ankle position, and so forth are positions at each of which the motion recognition device 20 is more suitably fastened to detect the physical exercise.

Please refer to FIG. 4A, FIG. 4B and FIG. 4C, which are schematic diagrams showing a physical exercise type recognized by the motion recognition device 20 fastened to a wrist. Please refer to FIG. 5, which is a schematic diagram showing a physical exercise type recognized by the motion recognition device 20 fastened to an upper arm. Please refer to FIG. 6, which is a schematic diagram showing a physical exercise type recognized by the motion recognition device 20 fastened to an upper arm. Please refer to FIG. 7A and FIG. 7B, which are schematic diagrams showing a physical exercise type recognized by the motion recognition device 20 fastened to an upper arm. Please refer to FIG. 8, which is a schematic diagram showing a physical exercise type recognized by the motion recognition device 20 fastened to an upper arm. Please refer to FIG. 9A and FIG. 9B, which are schematic diagrams showing a physical exercise type recognized by the motion recognition device 20 fastened to an ankle. Please refer to FIG. 10A and FIG. 10B, which are schematic diagrams showing a physical exercise type recognized by the motion recognition device 20 fastened to an ankle.

In some embodiments, the sensing unit 21 has a sensing orientation. The sensing unit 21 or the motion-sensing module has motion-sensing axis directions and respective sensing sensitivities in the motion-sensing axis directions, and senses the first body motion ML1 occurring at the specific position PL1 on the user's body 90. The user's body 90 has the specific body portion 911 at the specific position PL1. The motion-sensing module may be applied to sense different motions occurring at different body portions, such as the wrist, the upper arm and the ankle. When the motion-sensing module senses a specific motion occurring at the specific position PL1 on the user's body 90, the motion-sensing module has a highest sensing sensitivity in at least a motion-sensing axis direction corresponding to the specific position PL1. For instance, when sensing a wrist motion, the motion-sensing module has a highest sensing sensitivity in the X motion-sensing axis direction; therefore, the sense signal component level generated in the x motion-sensing axis direction is greater than that generated in either the y motion-sensing axis direction or the z motion-sensing axis direction. In some embodiments, the motion-sensing module outputs a first sense signal component, a second sense signal component and a third signal component in the respective x, y and z motion-sensing axis directions. For instance, the maximum levels of the first, the second and the third sense signal components, and the level domains of the first, the second and the third sense signal components are used to recognize the specific position PL1 or the specific body portion 911.

In some embodiments, the sensing unit 21 or the motion-sensing module is configured to have an arrangement orientation to change the sensing orientation of the sensing unit 21 when the specific position PL1 changes. The arrangement orientation may be changed to a different arrangement orientation when the specific position PL1 changes to a different position. For instance, in a specific state, when the motion recognition device 20 makes a decision that the z motion-sensing axis direction is the same as the gravity direction, the motion recognition device 20 recognizes the specific position PL1 as the wrist position, and is to recognize a wrist motion. In this specific state, when the motion recognition device 20 makes a decision that the x motion-sensing axis direction is the same as the gravity direction, the motion recognition device 20 recognizes the specific position PL1 as the upper arm position, and is to recognize an upper arm motion. In this specific state, when the motion recognition device 20 makes a decision that the negative x motion-sensing axis direction is the same as the gravity direction, the motion recognition device 20 recognizes the specific position PL1 as the ankle position, and is to recognize an ankle motion.

In some embodiments, the arrangement orientation of the motion-sensing module is arranged based on the specific position PL1. In some embodiments, in this specific state, the motion recognition device 20 detects an angle relationship between a specific motion-sensing axis direction of the motion-sensing module and the gravity direction to recognize the specific position PL1 as a body portion position. For instance, the motion recognition device 20 is configured to have the orientation KA1, the gravity direction QF1 and the body coordinate system UA1 used to determine the orientation KA1, and is fastened at the specific position PL1. In a state that the orientation KA1 is directed to a predetermined direction QH1 in relation to the gravity direction QF1, the processing unit 22 generates a specific position code CP1 representing the specific position PL1 based on the motion parameter signal structure SP1, and thereby recognizes the specific position PL1.

In some embodiments, any of the motion recognition devices 20, 30 and 40 serves as a wearable motion-sensing device, is fastened at a specific position PL1 on a user's body 91, generates a motion parameter signal structure SP1 by sensing a first body motion ML1 occurring at the specific position PL1, wherein the first body motion ML1 belongs to a first motion type HM1, and the specific position PL1 may be selected from a plurality of different positions, which include a wrist position, an upper arm position and an ankle position. The wearable motion-sensing device generates a specific position code CP1 representing the specific position PL1 based on the motion parameter signal structure SP1, determines a first candidate reference signal SR2 based on the motion parameter signal structure SP1 and the specific position code CP1, obtains a first motion characteristic value data unit DA2 from the motion parameter signal structure SP1 based on the first candidate reference signal SR2, and recognizes the first motion type HM1 to obtain a motion type code CT1 representing the first motion type HM1 based on the first motion characteristic value data unit DA2, so that the wearable motion-sensing device recognizes a motion direction of the first body motion ML1, and count motion cycles of the first body motion ML1.

The wearable motion-sensing device recognizes the first motion type HM1 by performing a first motion recognition algorithm. The sensing unit 21 includes a six-axis inertial sensing component. For instance, the sensing unit 21 includes an accelerometer 211 being a three-axis accelerometer, and a gyroscope 212 being a three-axis gyroscope. The wearable motion-sensing device, by using the sensing unit 21, generates the sense signal SE1 in response to the first body motion ML1 being a physical exercise, and automatically recognizes the specific position PL1 and the first motion type HM1 based on the sense signal SE1 by performing the first motion recognition algorithm. For instance, the user's body 91 has a specific body portion 911 at the specific position PL1, and any of the motion recognition devices 20, 30 and 40 is fastened to the specific body portion 911.

The first motion recognition algorithm includes sense signal processing, fastening position recognition and motion type recognition. The motion type recognition includes the following features to determine the first candidate reference signal SR2, obtain the first motion characteristic value data unit DA2, decide whether the first body motion ML1 satisfies a periodic-motion start condition or a periodic-motion termination condition, and perform a calculation to recognize the first motion type HM1 based on the first characteristic function code data unit F1. For instance, the processing unit 22 performs the first motion recognition algorithm. For instance, the converting unit 411 and the processing unit 42 perform the first motion recognition algorithm. In the following description, it is taken as an example that the processing unit 22 performs the first motion recognition algorithm.

Figure 11:
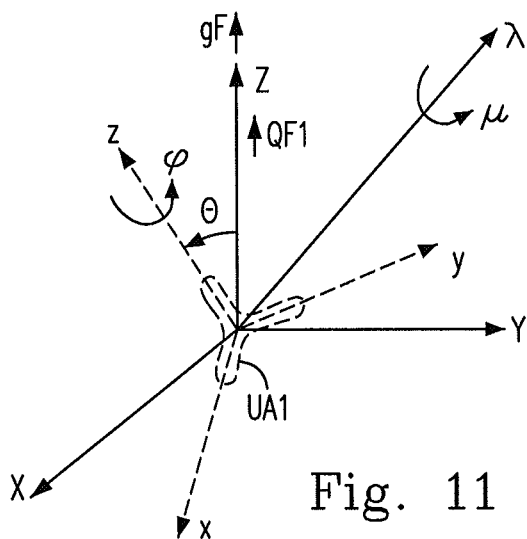
FIG. 11 is a schematic diagram showing reference coordinate systems according to various embodiments of the present disclosure.

Please refer to FIG. 11, which is a schematic diagram showing reference coordinate systems according to various embodiments of the present disclosure. Please additionally refer to FIG. 1. FIG. 11 shows a reference coordinate system having three reference coordinate axes X, Y and Z, and the body coordinate system UA1 having three reference coordinate axes x, y and z. The body coordinate system UA1 is expressed in relation to the gravity direction QF1. The processing unit 22 receives the sense signal SE1, which is generated in relation to the body coordinate system UA1.

The accelerometer 211 of the sensing unit 21 generates the accelerometer signal SE11 (or a first signal $\vec{a}*_{acc}$). The gyroscope 212 of the sensing unit 21 generates the gyroscope signal SE12 (or a second signal $\vec{\omega}*_{gyro}$). The sense signal SE1 includes the first signal $\vec{a}*_{acc}$ and the second signal $\vec{\omega}*_{gyro}$. The first signal $\vec{a}*_{acc}$ includes three original sense signal components $a*_{acc,x}$, $a*_{acc,y}$ and $a*_{acc,z}$ respectively in relation to the three reference coordinate axes x, y and z. The second signal $\vec{\omega}*_{gyro}$ includes three original sense signal components $\omega*_{acc,x}$, $\omega*_{acc,y}$ and $\omega*_{acc,z}$ respectively in relation to the three reference coordinate axes x, y and z. The first signal $\vec{a}*_{acc}$ includes a gravitational acceleration signal component $\vec{g}*_{acc}$. By using a six-axis fusion algorithm (or a signal fusion operation), the processing unit 22 obtains the motion parameter signal structure SP1 including a quaternion $(q_0, q_1, q_2, q_3)$, an estimated roll angle $\varphi_{Roll}$ associated with a Euler angle, an estimated pitch angle $\theta_{pitch}$ associated with a Euler angle, a filtered third signal $\vec{a}_{acc}^{f}$, and a filtered fourth signal $\vec{\omega}_{gyro}^{f}$. For instance, the processing unit 22 performs a first filter operation on the first signal $\vec{a}*_{acc}$ to generate the third signal $\vec{a}_{acc}^{f}$, and performs a second filter operation on the second signal $\vec{\omega}*_{gyro}$ to generate the fourth signal $\vec{\omega}_{gyro}^{f}$.

The estimation of a roll angle φ of the body coordinate system UA1 is expressed in the following equation.

$$\varphi_{Roll} = \tan^{-1}(g_y/g_z)$$ Equation 1

The estimation of a pitch angle θ of the body coordinate system UA1 is expressed in the following equation.

$$\theta_{Pitch} = \tan^{-1}(g_x/\sqrt{g_y^2+g_z^2})$$ Equation 2

The quaternion $(q_0, q_1, q_2, q_3)$ is expressed in the following equation.

$$\tilde{Q} = q_0 + \vec{i}\, q_1 + \vec{j}\, q_2 + \vec{k}\, q_3$$

$$q_0 = \cos(u/2);\ q_1 = \lambda_1 \sin(u/2);\ q_2 = \lambda_2 \sin(u/2);\ q_3 = \lambda_3 \sin(u/2)$$

$$\lambda_1 = \vec{\lambda} \cdot \vec{x};\ \lambda_2 = \vec{\lambda} \cdot \vec{y};\ \lambda_3 = \vec{\lambda} \cdot \vec{z}$$

The quaternion $(q_0, q_1, q_2, q_3)$ should satisfy a normalization constant thereof.

$$q_0^2 + q_1^2 + q_2^2 + q_3^2 = 1$$

When an object continuously moves, the quaternion ($q_0$, $q_1$, $q_2$, $q_3$) and a measured angular body velocity satisfy the following relationship.

$$\dot{q}_{4\times 1} = \frac{1}{2\|q\|} \begin{bmatrix} -q_1 & -q_2 & -q_3 \\ q_0 & -q_3 & q_2 \\ q_3 & q_0 & -q_1 \\ -q_2 & q_1 & q_0 \end{bmatrix} \begin{bmatrix} \omega_{gyro,x} \\ \omega_{gyro,y} \\ \omega_{gyro,z} \end{bmatrix} \quad \text{Equation 3}$$

When the motion recognition device 20 makes a rotation including a yaw, a pitch and a roll which are sequentially made, the transformation relation from the quaternion ($q_0$, $q_1$, $q_2$, $q_3$) to estimated Euler angles (including an estimated roll angle $\varphi_{Roll}$, an estimated pitch angle $\theta_{Pitch}$ and an estimated yaw angle $\psi_{Yaw}$) is listed as follows.

$$\varphi_{Roll} = \tan^{-1}\left(\frac{2(q_2 q_3 + q_0 q_1)}{q_0^2 - q_1^2 - q_2^2 + q_3^2}\right) \quad \text{Equation 4}$$

$$\theta_{Pitch} = \sin^{-1}(2(-q_1 q_3 + q_0 q_2))$$

$$\psi_{Yaw} = \tan^{-1}\left(\frac{2(q_1 q_2 + q_0 q_3)}{q_0^2 + q_1^2 - q_2^2 - q_3^2}\right)$$

When the motion recognition device 20 makes the rotation, the transformation relation from the estimated Euler angles to the quaternion ($q_0$, $q_1$, $q_2$, $q_3$) is listed as follows.

$q_0 = \cos(\varphi_{Roll}/2)\cos(\theta_{Pitch}/2)\cos(\psi_{Yaw}/2) + \sin(\varphi_{Roll}/2)\sin(\theta_{Pitch}/2)\sin(\psi_{Yaw}/2)$ $q_1 = \sin(\varphi_{Roll}/2)\cos(\theta_{Pitch}/2)\cos(\psi_{Yaw}/2) - \cos(\varphi_{Roll}/2)\sin(\theta_{Pitch}/2)\sin(\psi_{Yaw}/2)$ $q_2 \cos(\varphi_{Roll}/2)\sin(\theta_{Pitch}/2)\cos(\psi_{Yaw}/2) + \sin(\varphi_{Roll}/2)\cos(\theta_{Pitch}/2)\sin(\psi_{Yaw}/2)$ $q_3 = \cos(\varphi_{Roll}/2)\cos(\theta_{Pitch}/2)\sin(\psi_{Yaw}/2) - \sin(\varphi_{Roll}/2)\sin(\theta_{Pitch}/2)\cos(\psi_{Yaw}/2)$ Equation 5

By employing a specific fusion algorithm architecture such as an extended Kalman filter with the function of Equations 1-5, the processing unit 22 obtains the motion parameter signal structure SP1. In other words, the processing unit 22 processes the sense signal SE1 to generate the motion parameter signal structure SP1. The motion parameter signal structure SP1 includes a plurality of motion parameter signals SP11, SP12, SP13, . . . SP18 and SP19, which include the third signal $\bar{a}_{acc}^f$, the fourth signal $\bar{\omega}_{gyro}^f$, a signal of the estimated roll angle $\varphi_{Roll}$, a signal of the estimated pitch angle $\theta_{Pitch}$, and a signal of the quaternion ($q_0$, $q_1$, $q_2$, $q_3$). For instance, motion parameter signal structure SP1 is generated by using the signal fusion operation.

Figure 12:
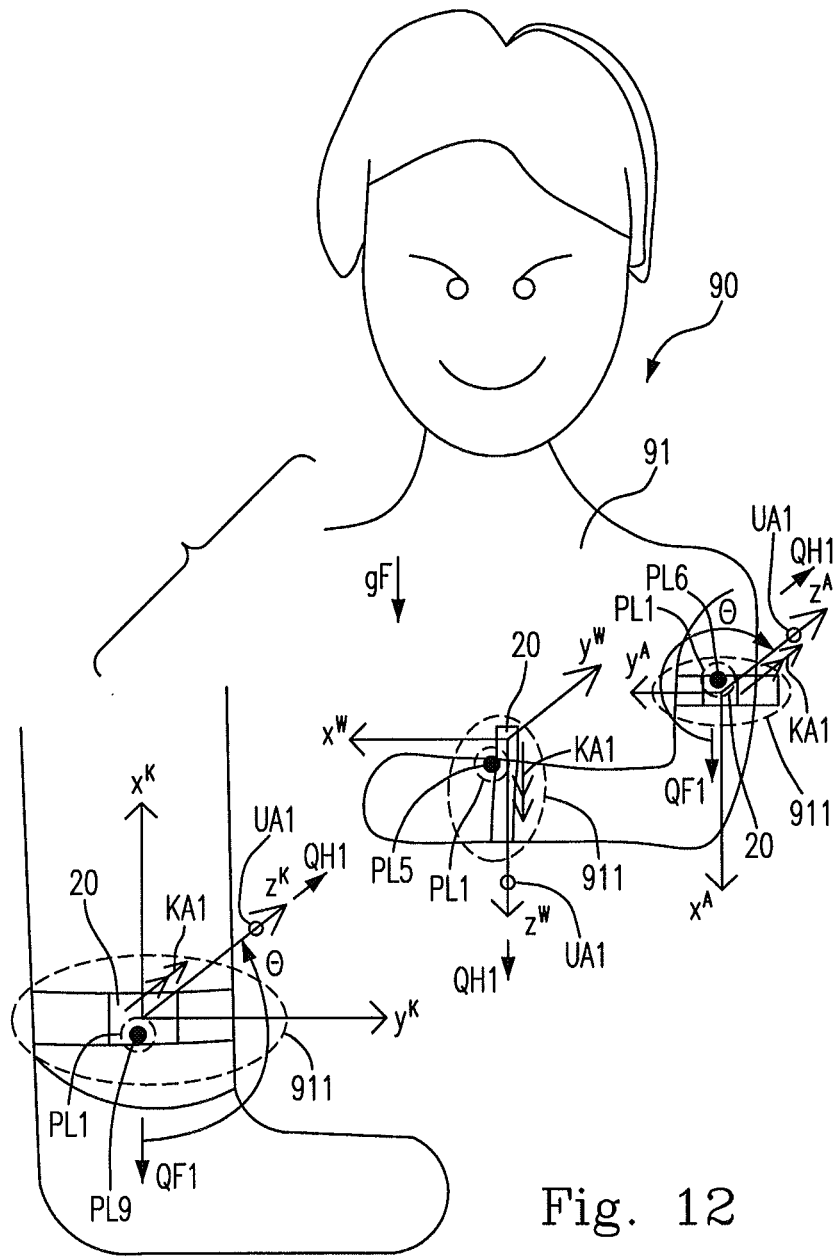
FIG. 12 is a schematic diagram showing the relationship between the motion recognition device and the user's body illustrated in FIG. 2.

Please refer to FIG. 12, which is a schematic diagram showing the relationship between the motion recognition device 20 and the user's body 91 illustrated in FIG. 2. According to the muscle groups mainly trained with physical exercises, a plurality of physical exercise types are divided into a plurality of physical exercise type groups, which respectively correspond to the plurality of different positions PL5, PL6, . . . PL9. For instance, the three positions PL5, PL6 and PL9 are respectively predetermined to be the wrist position, the upper arm position and the ankle position. In a specific state, the orientation KA1 of the motion recognition device 20 is directed to a first predetermined direction when the motion recognition device 20 is fastened at position PL5; in a specific state, the orientation KA1 of the motion recognition device 20 is directed to a second predetermined direction when the motion recognition device 20 is fastened at position PL6; and in a specific state, the orientation KA1 of the motion recognition device 20 is directed to a third predetermined direction when the motion recognition device 20 is fastened at position PL9.

The first, the second and the third predetermined directions are different in relation to the gravity direction QF1, and may be determined according to a design arrangement, wherein the design arrangement is provided by most meeting the user 90 with the operation situation, the operation habit and the ergonomic principle. The specific position PL1 is selected from the plurality of different positions PL5, PL6, . . . PL9 on the user's body 91. For the first body motion ML1 occurring at the specific position PL1, in a state that the orientation KA1 is directed in a predetermined direction QH1 in relation to the gravity direction QF1, the processing unit 22 generates a specific position code CP1 representing the specific position PL1 based on the motion parameter signal structure SP1, and thereby recognizes the specific position PL1.

In FIG. 12, the motion recognition device 20 has the body coordinate system UA1 used to determine the orientation KA1. When the motion recognition device 20 is fastened at position PL5 (the wrist position), the three reference axes x, y and z of the body coordinate system UA1 are respectively expressed by three reference axes $x^W$, $y^W$ and $z^W$. When the motion recognition device 20 is fastened at position PL6 (the upper arm position), the three reference axes x, y and z of the body coordinate system UA1 are respectively expressed by three reference axes $x^A$, $y^A$ and $z^A$. When the motion recognition device 20 is fastened at position PL9 (the ankle position), the three reference axes x, y and z of the body coordinate system UA1 are respectively expressed by three reference axes $x^K$, $y^K$ and $z^K$.

For instance, the motion recognition device 20 has a gravitational acceleration gF, which has a gravitational acceleration direction the same as the gravity direction QF1. The third signal $\bar{a}_{acc}^f$ has a gravitational acceleration signal component $\bar{g}_{acc}^f$, which is associated with the gravitational acceleration gF or the gravitational acceleration signal component $\bar{g}*_{acc}$, and is a three-axis signal. The processing unit 22 regards the gravity direction QF1 as the principal reference axis direction, and obtains the specific position code CP1 by mainly using the gravitational acceleration signal component $\bar{g}_{acc}^f$. When the motion recognition device 20 additionally employs at least one selected from a group consisting of the estimated pitch angle $\theta_{Pitch}$, the estimated roll angle $\varphi_{Roll}$ and the quaternion ($q_0$, $q_1$, $q_2$, $q_3$), which are generated through the six-axis signal fusion operation, the recognition precision of the specific position PL1 is increased. For instance, the predetermined direction QH1 (or the reference axis of the body coordinate system UA1) and the gravity direction QF1 have the first angle θ (or a pitch angle) therebetween.

As shown in FIG. 12, the user's body 91 has the specific body portion 911 at the specific position PL1, wherein the specific body portion 911 has the first body motion ML1, and may be the wrist, the upper arm or the ankle. The motion recognition device 20 further includes a push button 23 coupled to the processing unit 22. In the state that the orientation KA1 is directed to the predetermined direction QH1 in relation to the gravity direction QF1, the push button 23 provides a trigger signal ST1 in response to a user button-press from the user 90, and the processing unit 22 makes a first decision on whether the processing unit 22 detects the trigger signal ST1. For instance, when the first decision is positive, the processing unit 22 obtains the specific position code CP1 based on the gravitational acceleration signal component $\bar{g}_{acc}^{f}$ or a signal of the estimated pitch angle $\theta_{Pitch}$. For instance, a signal of the estimated angle SK1 is the signal of the estimated pitch angle $\theta_{Pitch}$.

The processing unit 22 obtains a recognition reference data unit DR based on the specific position code CP1. The recognition reference data unit DR is predetermined based on the plurality of principal motion axis direction data units DQ1, DQ2, . . . DQ6, and includes a candidate reference signal code data unit CA and a motion type indicator data unit CH. The candidate reference signal code data unit CA includes a first candidate reference signal code CA2. The first candidate reference signal code CA2 represents a first candidate reference signal SR2 derived from the motion parameter signal structure SP1. The motion type indicator data unit CH includes a motion type indicator CH2 corresponding to the first candidate reference signal code CA2. The motion type indicator CH2 indicates one of an invalid motion type and a second motion type HM2 included in the plurality of motion types HA1, HA2, . . . HA6. The processing unit 22 determines the first candidate reference signal SR2 based on the motion parameter signal structure SP1 and the first candidate reference signal code CA2.

In some embodiments, according to the ergonomic principle, a plurality of recognition reference data units corresponds to the plurality of different positions PL5, PL6, . . . PL9 are different. When the specific position code CP1 and the recognition reference data unit DR are obtained, the processing unit 22 finishes a first stage of recognition. The processing unit 22 determines at least one candidate reference signal based on the motion parameter signal structure SP1 and the recognition reference data unit DR, wherein the at least one candidate reference signal may include an effective reference signal. For instance, the processing unit 22 determines the following candidate reference signals based on the third signal $\bar{a}_{acc}^{f}$, the fourth signal $\bar{\omega}_{gyro}^{f}$, the signal of the estimated roll angle $\varphi_{Roll}$, the signal of the estimated pitch angle $\theta_{Pitch}$, the signal of the quaternion ($q_0$, $q_1$, $q_2$, $q_3$), and the candidate reference signal code data unit CA.

$\text{Ref}_i(\bar{a}_{acc}^{f}, \bar{\omega}_{gyro}^{f}, \varphi_{Roll}, \theta_{Pitch}, (q_0, q_1, q_2, q_3))$, wherein the symbol i is equal to one of 1 to 3; the symbol i with the value of 1 represents the wrist position; the symbol i with the value of 2 represents the upper arm position; and the symbol i with the value of 3 represents the ankle position.

In some embodiments, the first candidate reference signal SR2 represented by the first candidate reference signal code CA2 is one of the candidate reference signals $\text{Ref}_i(\bar{a}_{acc}^{f}, \bar{\omega}_{gyro}^{f}, \varphi_{Roll}, \theta_{Pitch}, (q_0, q_1, q_2, q_3))$. The processing unit 22 obtains a first motion characteristic value data unit DA2 from the motion parameter signal structure SP1 based on the first candidate reference signal SR2. For instance, the first body motion ML1 is a reciprocating motion, and includes a first motion portion ML11 forming a first motion cycle W1. The third signal $\bar{a}_{acc}^{f}$ being a three-axis signal has a first signal portion corresponding to the first body motion ML1, and the fourth signal $\bar{\omega}_{gyro}^{f}$ being a three-axis signal has a second signal portion corresponding to the first body motion ML1. The processing unit 22 obtains characteristic values with a count number N from the first and the second signal portions based on the one of the candidate reference signals $\text{Ref}_i(\bar{a}_{acc}^{f}, \bar{\omega}_{gyro}^{f}, \varphi_{Roll}, \theta_{Pitch}, (q_0, q_1, q_2, q_3))$, wherein N is greater than 1. For instance, the N characteristic values include the maximum values and the minimum values of the third signal $\bar{a}_{acc}^{f}$, the fourth signal $\bar{\omega}_{gyro}^{f}$, the signal of the estimated roll angle $\varphi_{Roll}$, the signal of the estimated pitch angle $\theta_{pitch}$, and the signal of the quaternion ($q_0$, $q_1$, $q_2$, $q_3$), and are expressed by $C_{i\sim N}$: $C_{i\sim N}(\bar{a}_{acc}^{f}, \bar{\omega}_{gyro}^{f}, \varphi_{Roll}, \theta_{Pitch}, (q_0, q_1, q_2, q_3))$.

Figure 13:
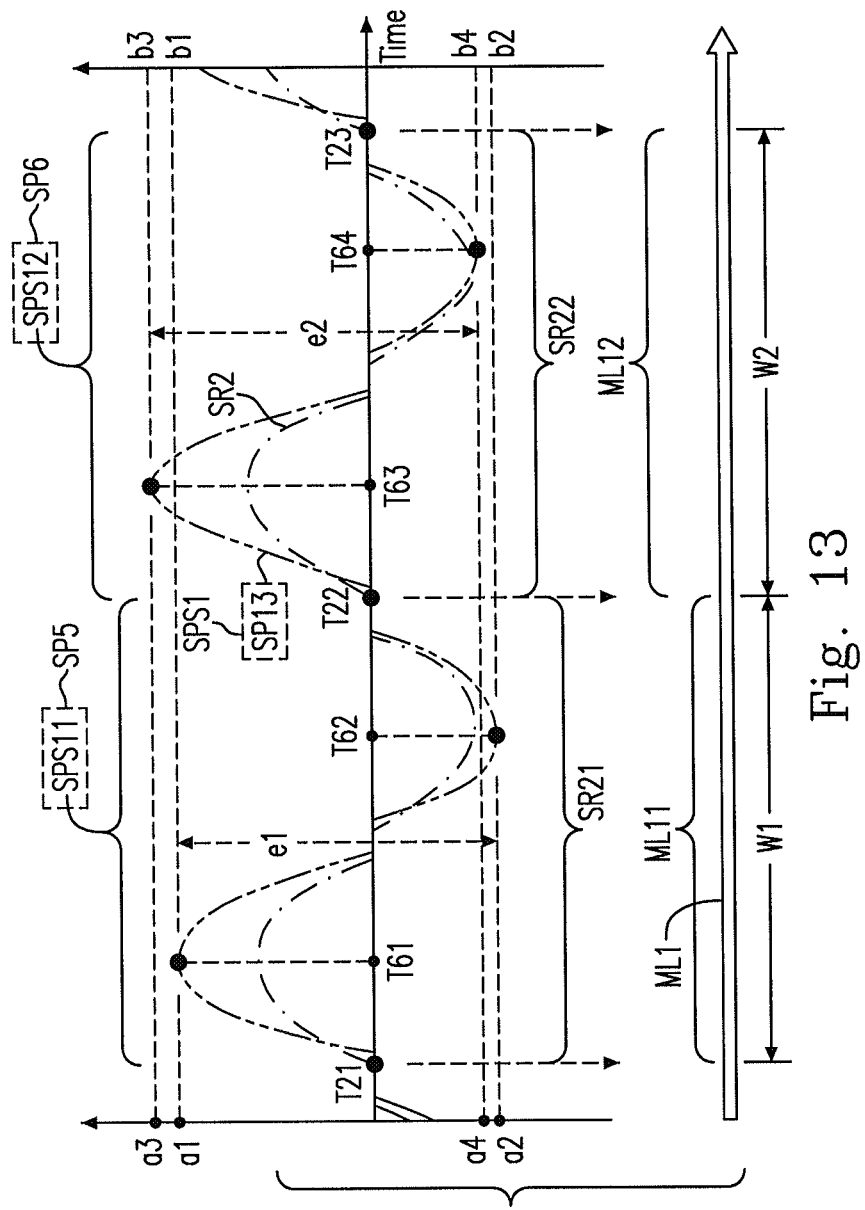
FIG. 13 is a schematic diagram showing a first candidate reference signal and a representative signal of the motion recognition device illustrated in FIG. 1.

Please refer to FIG. 13, which is a schematic diagram showing the first candidate reference signal SR2 and the representative signal SPS1 of the motion recognition device 20 illustrated in FIG. 1. In some embodiments, the processing unit 22, based on the first candidate reference signal SR2, decides whether the first body motion ML1 effectively starts or effectively terminates. After the trigger signal ST1 is provided, the first body motion ML1 includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. The motion parameter signal structure SP1 includes a first motion parameter signal structure portion SP5 and a second motion parameter signal structure portion SP6 respectively corresponding to the first and the second motion portions ML11 and ML12. The first candidate reference signal SR2 includes a first candidate reference signal portion SR21 and a second candidate reference signal portion SR22 respectively corresponding to the first and the second motion portions ML11 and ML12, wherein the second candidate reference signal portion SR22 is adjacent to the first candidate reference signal portion SR21.

The first motion characteristic value data unit DA2 includes a first motion characteristic value data unit portion DA21 and a second motion characteristic value data unit portion DA22 respectively corresponding to the first and the second motion portions ML11 and ML12. The processing unit 22 obtains the first motion characteristic value data unit portion DA21 from the first motion parameter signal structure portion SP5 based on the first candidate reference signal portion SR21. The processing unit 22 obtains the second motion characteristic value data unit portion DA22 from the second motion parameter signal structure portion SP6 based on the second candidate reference signal portion SR22. The processing unit 22, based on the first and the second motion characteristic value data unit portions DA21 and DA22, decides whether the first body motion ML1 has effectively started. For instance, the processing unit 22 generates a difference data unit DC1 based on the first and the second motion characteristic value data unit portions DA21 and DA22, and makes the second decision on whether the difference data unit DC1 satisfies the first specific condition for a periodic-motion start decision. When the second decision is positive, the processing unit 22 recognizes the effective reference signal SRP as the first candidate reference signal SR2, and determines that the first body motion ML1 satisfies a predetermined periodic-motion start condition. For instance, the second motion cycle ML12 is later than the first motion cycle ML11; and the second motion characteristic value data unit portion DA22 includes a plurality of specific motion characteristic values.

In the prior art, the decision regarding each of the periodic-motion start and the periodic-motion termination usually uses "motion at rest" as a reference indicator. However, human body motions are too numerous to enumerate. If the condition of the "motion at rest" is only used as a decision condition, it is easy to result in the specific purpose of the nonuser or the motion product, thus generating the inevitable misjudgement. In some embodiments, the processing unit 22 obtains a first plurality of specific characteristic values $C_{M2,i\sim n}$ and a second plurality of specific characteristic values $C_{M2,i\sim n}$ respectively on the two adjacent motion cycles W1 and W2, and performs a comparison to obtain a difference between the first and the second plurality of specific characteristic values $C_{M2,i\sim n}$ and $C_{M2,i\sim n}$. For instance, the first and the second motion characteristic value data unit portions DA21 and DA22 respectively include the first and the second plurality of specific characteristic values $C_{M2,i\sim n}$ and $C_{M2,i\sim n}$. When each of characteristic value differences $\Delta C_{N2\sim Mi,i\sim n}$ of the first and the second plurality of specific characteristic values $C_{M2,i\sim n}$ and $C_{M2,i\sim n}$ falls within a corresponding threshold value range $\xi_{i\sim n}$, the processing unit 22 determines that the first and the second plurality of specific characteristic values $C_{M2,i\sim n}$ and $C_{M2,i\sim n}$ can be applied to a main recognition function to perform a motion type recognition for the first body motion ML1. After finishing the motion type recognition for the first body motion ML1, when an additional obtained characteristic value difference falls outside a corresponding threshold value range $\xi'_{i\sim n}$, the processing unit 22 determines that the first body motion ML1 has terminated.

As shown in FIG. 13, the first body motion ML1 has the first motion portion ML11 between the time T21 and the time T22, and has the second motion portion ML12 between the time T22 and the time T23. The first motion portion ML11 forms the first motion cycle W1 between the time T21 and the time T22; and the second motion portion ML12 forms the second motion cycle W2 between the time T22 and the time T23. The first candidate reference signal portion SR21 corresponding to the first motion portion ML11 forms a first signal cycle between the time T21 and the time T22; and the second candidate reference signal portion SR22 corresponding to the second motion portion ML12 forms a second signal cycle between the time T22 and the time T23.

For instance, the representative signal SPS1 is the motion parameter signal SP13 in the motion parameter signal structure SP1, has a first motion parameter signal portion SPS11 between the time T21 and the time T22, and has a second motion parameter signal portion SPS12 between the time T22 and the time T23. The first motion parameter signal structure portion SP5 includes the first motion parameter signal portion SPS11; and the second motion parameter signal structure portion SP6 includes the second motion parameter signal portion SPS12.

The first motion characteristic value data unit portion DA21 includes a first motion characteristic value data unit sub-portion DA21A corresponding to the representative signal SPS1 (such as the motion parameter signal SP13). The second motion characteristic value data unit portion DA22 includes a second motion characteristic value data unit sub-portion DA22A corresponding to the representative signal SPS1. The processing unit 22 obtains the first motion characteristic value data unit sub-portion DA21A from the first motion parameter signal portion SPS11 based on the first candidate reference signal portion SR21, and obtains the second motion characteristic value data unit sub-portion DA22A from the second motion parameter signal portion SPS12 based on the second candidate reference signal portion SR22.

The first motion characteristic value data unit sub-portion DA21A includes a motion characteristic value a1 at the time T61, and a motion characteristic value a2 at the time T62. The second motion characteristic value data unit sub-portion DA22A includes a motion characteristic value a3 at the time T63, and a motion characteristic value a4 at the time T64. For instance, each of the motion characteristic values a1 and a3 is a maximum value; and each of the motion characteristic values a2 and a4 is a minimum value. The first motion characteristic value data unit sub-portion DA21A has a first maximum value b1, a first minimum value b2, and a first difference e1 between the first maximum value b1 and the first minimum value b2. The second motion characteristic value data unit sub-portion DA22A has a second maximum value b3, a second minimum value b4, and a second difference e2 between the second maximum value b3 and the second minimum value b4. For instance, the first and the second maximum values b1 and b3 are respectively the motion characteristic values a1 and a3; and the first and the second minimum values b2 and b4 are respectively the motion characteristic values a2 and a4.

In some embodiments, the processing unit 22 obtains a representative extreme value deviation DC11 between the first and the second motion characteristic value data unit portions DA21 and DA22 by comparing the first motion characteristic value data unit portion DA21 with the second motion characteristic value data unit portion DA22. For instance, the representative extreme value deviation DC11 is a maximum one selected from a group consisting of an absolute value |a2−a1|, . . . and an absolute value |a4−a3|. The processing unit 22 obtains a representative value difference DC12 from the first and the second differences e1 and e2. The difference data unit DC1 includes the representative extreme value deviation DC11 and the representative value difference DC12. The first specific condition includes a first sub-condition and a second sub-condition. The first sub-condition is that the representative extreme value deviation DC11 falls within a first predetermined value range. The second sub-condition is that the representative value difference DC12 falls within a second predetermined value range.

Figure 14:
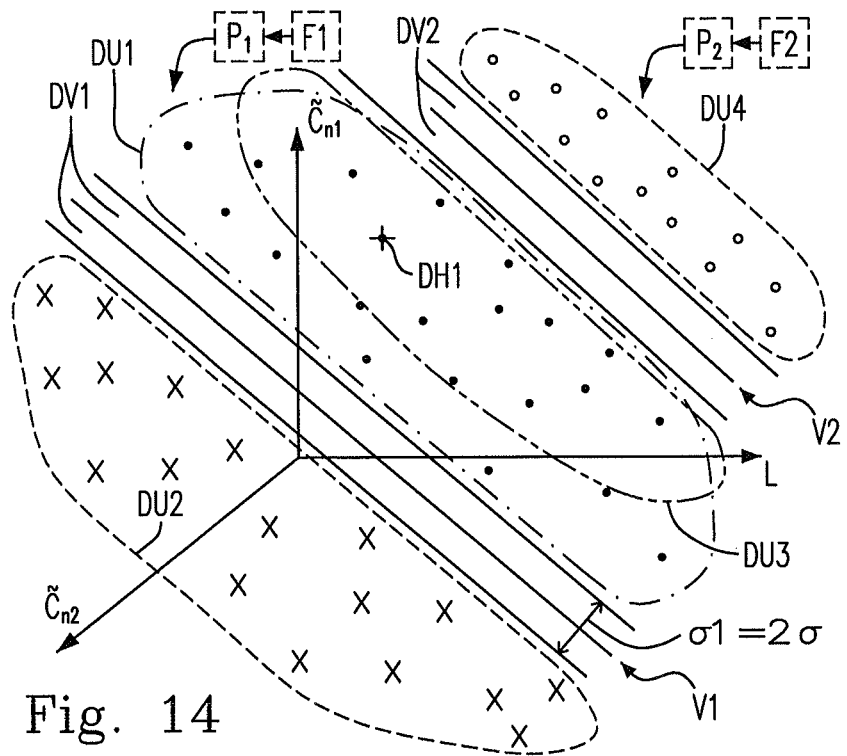
FIG. 14 is a schematic diagram showing a motion type recognition of a first body motion according to various embodiments of the present disclosure.

Please refer to FIG. 14, which is a schematic diagram showing a motion type recognition of the first body motion ML1 according to various embodiments of the present disclosure. In some embodiments, the processing unit 22 provides beforehand the first characteristic function code data unit F1, which is associated with the first candidate reference signal code CA2 and a first plurality of recognition value domains DU1, DU2 and DV1. The first characteristic function code data unit F1 is employed to indicate one of the first plurality of recognition value domains DU1, DU2 and DV1. The first plurality of recognition value domains DU1, DU2 and DV1 include a first recognition value domain DU1, a second recognition value domain DU2 adjacent to the first recognition value domain DU1, and a first confidence value domain DV1 between the first and the second recognition value domains DU1 and DU2. For instance, the first confidence value domain DV1 is optional. The first and the second recognition value domains DU1 and DU2 respectively indicate the third motion type H1 and the fourth motion type H2. For instance, the first confidence value domain DV1 has a confidence value distance σ1 between the first and the second recognition value domains DU1 and DU2. The first characteristic function code data unit F1 represents a motion type cut function $P_1$ employed to indicate the one of the first plurality of recognition value domains DU1, DU2 and DV1, and is expressed based on a relationship among the plurality of specific motion characteristic values.

After the second decision on whether the difference data unit DC1 satisfies the first specific condition is positive, the processing unit 42 performs a first calculation to generate a recognition value DH1 based on the first characteristic function code data unit F1 and the second motion characteristic value data unit portion DA22, determines an effective recognition value domain DUA in the first and the second recognition value domains DU1 and DU2 that the recognition value DH1 belongs to, recognizes the first motion type HM1 as an effective motion type indicated by the effective recognition value domain DUA, and obtains a motion type code CT1 corresponding to the effective recognition value domain DUA. The motion type code CT1 represents the first motion type HM1. The processing unit 22 generates a motion measurement information DM1 associated with the first body motion ML1 based on the motion type code CT1.

In some embodiments, the processing unit 22 provides a set of characteristic function code data units F1, F2, and so forth beforehand respectively representing a set of motion type cut functions $P_{1 \sim K}$, which is established by calculating large volumes of data. For instance, the processing unit 22 performs a calculation to effectively recognize the first motion type HM1 based on at least one selected from the set of characteristic function code data units F11, F12, and so forth and the second plurality of specific characteristic values $C_{M2,i \sim n}$. The set of motion type cut functions $P_{1 \sim K}$ has a set of cut planes and a hierarchy number K, wherein K is a natural number. When K is greater than 1, the set of motion type cut functions is arranged according to an order, and is at least partially employed to recognize the first motion type HM1. For instance, the set of motion type cut functions $P_{1 \sim K}$ includes linear or nonlinear multi-dimensional characteristic functions, which are trained based on a first plurality of motion characteristic values $C_{M1,1 \sim N}^{L}$ and a second plurality of motion characteristic values $C_{M2,1 \sim N}^{L}$, wherein L represents the record number of motion characteristic values in the database to establish the set of motion type cut functions $P_{1 \sim K}$. For instance, the set of motion type cut functions $P_{1 \sim K}$ is expressed as follows.

$P_i = F(\tilde{C}_{M1,1 \sim N}, \tilde{C}_{M2,1 \sim N}) \pm \sigma$, $i=1 \sim K$, wherein $\sigma$ represents a threshold distance of a confidence value domain. For instance, the confidence value distance $\sigma 1$ of the first confidence value domain DV1 is equal to $2\sigma$.

As shown in FIG. 14, the first and the second recognition value domains DU1 and DU2 respectively indicate the third motion type H1 and the fourth motion type H2, and are two-dimensional recognition value domains. The motion type cut functions $P_1$ has a cut plane V1, which separates the first recognition value domains DU1 from the second recognition value domain DU2. The motion type cut functions $P_2$ has a cut plane V2, which separates the third recognition value domain DU3 from the fourth recognition value domain DU4. For instance, the first and the second characteristic function code data units F1 and F2 may respectively represent the motion type cut functions $P_1$ and $P_2$.

Figure 15:
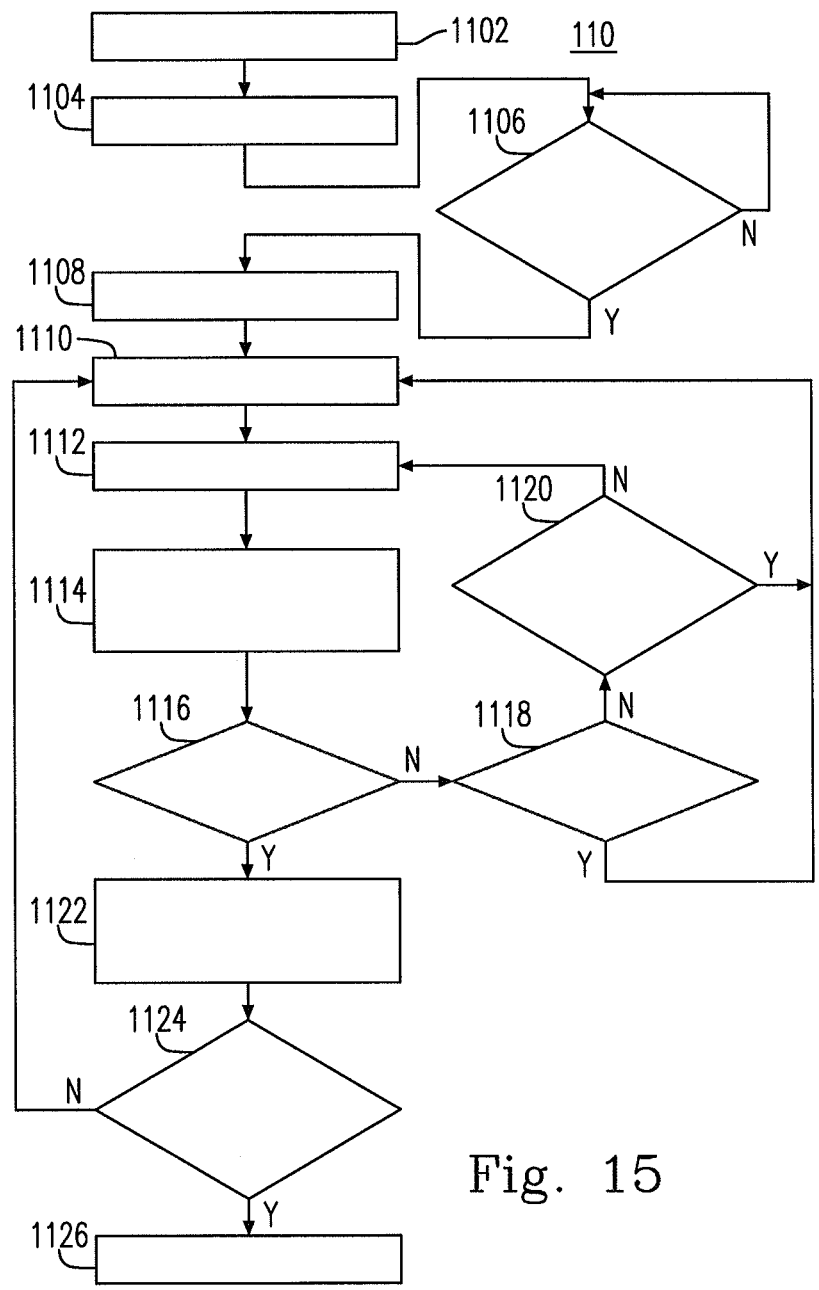
FIG. 15 is a schematic diagram showing a flow of a first motion type recognition algorithm according to various embodiments of the present disclosure.

Please refer to FIG. 15, which is a schematic diagram showing a flow of a first motion type recognition algorithm 110 according to various embodiments of the present disclosure. In step 1102, the sensing unit 21 generates a sense signal SE1 in response to a first body motion ML1 occurring at a specific position PL1 on a user's body 91. The first body motion ML1 belongs to a first motion type HM1; and the sense signal is generated in relation to a body coordinate system UA1 of the sensing unit 21.

In step 1104, the processing unit 22 or the converting unit 411 processes the sense signal SE1 to generate a motion parameter signal structure SP1, wherein the sense signal SE1 includes an accelerometer signal SE11 and a gyroscope signal SE12, and the motion parameter signal structure SP1 can include a fusion signal SPS0 of the accelerometer signal SE11 and the gyroscope signal SE12.

In step 1106, the processing unit 22 makes a first decision on whether the processing unit 22 detects a trigger signal ST1. When the first decision is negative, the step after step 1106 returns to step 1106. When the first decision is positive, the step after step 1106 is step 1108.

In step 1108, the processing unit 22 generates a specific position code CP1 representing the specific position PL1 based on the motion parameter signal structure SP1. The user's body 91 wears the motion recognition device 20 at the specific position PL1, wherein the motion recognition device 20 includes the body coordinate system UA1, the sensing unit 21 and the processing unit 22.

In step 1110, the processing unit 22 obtains a recognition reference data unit DR based on the specific position code CP1. The recognition reference data unit DR is predetermined based on the body coordinate system UA1 and a principal motion axis direction of the first motion type HM1, and includes a first candidate reference signal code CA2. The first candidate reference signal code CA2 represents a first candidate reference signal SR2 derived from the motion parameter signal structure SP1. The processing unit 22 determines the first candidate reference signal SR2 based on the motion parameter signal structure SP1 and the first candidate reference signal code CA2.

In step 1112, the processing unit 22 obtains a first motion characteristic value data unit DA2 from the motion parameter signal structure SP1 based on the first candidate reference signal SR2. The first body motion ML1 includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. The first motion characteristic value data unit DA2 includes a first motion characteristic value data unit portion DA21 and a second motion characteristic value data unit portion DA22 respectively corresponding to the first and the second motion portions ML11 and ML12.

In step 1114, the processing unit 22 generates a difference data unit DC1 based on the first and the second motion characteristic value data unit portions DA21 and DA22, and employs the difference data unit DC1 to decide whether the first body motion ML1 has effectively terminated or started. The difference data unit DC1 includes a representative extreme value deviation DC11, which is generated by comparing the first motion characteristic value data unit portion DA21 with the second motion characteristic value data unit portion DA22.

In step 1116, the processing unit 22 makes a second decision on whether the difference data unit DC1 satisfies a first specific condition for a periodic-motion start decision. When the second decision is negative, the step after step 1116 is step 1118. When the second decision is positive, the step after step 1116 is step 1122.

In step 1118, the processing unit 22 makes a third decision on whether the difference data unit DC1 satisfies a second specific condition for a motion termination decision. When the third decision is negative, the step after step 1118 is step 1120. When the third decision is positive, the step after step 1118 returns to step 1110.

In step 1120, the processing unit 22 makes a fourth decision on whether a current negative decision number of the third decision reaches a predetermined threshold number. When the fourth decision is negative, the step after step 1120 returns to step 1112. When the fourth decision is positive, the step after step 1120 returns to step 1110. For instance, when the predetermined threshold number is equal to 1, the fourth decision is made only once to be positive.

In step 1122, the processing unit 22 recognizes the effective reference signal SRP as the first candidate reference signal SR2, determines that the first body motion ML1 satisfies a predetermined periodic-motion start condition, and performs a calculation to recognize the first motion type HM1 based on at least a first characteristic function code data unit F1 and the second motion characteristic value data unit portion DA22.

In step 1124, the processing unit 22 makes a fifth decision on whether it is successful to recognize the first motion type HM1 by performing the calculation. When the fifth decision is negative, the step after step 1124 returns to step 1110. When the fifth decision is positive, the step after step 1124 is step 1126.

In step 1126, the processing unit 22 obtains a motion type code CT1 representing the first motion type HM1, and generates a motion measurement information DM1 associated with the first body motion ML1 based on the motion type code CT1.

In various embodiments disclosed according to the illustrations in FIGS. 1, 2 and 3, any of the motion recognition devices 20, 30 and 40 employs the sensing unit 21, serving as a six-axis inertial sensing component, to implement the motion type recognition. The sensing unit 21 includes an accelerometer 211 being a three-axis accelerometer, and a gyroscope 212 being a three-axis gyroscope. For many known physical exercise types commonly seen at a fitness center, any of the motion recognition devices 20, 30 and 40 automatically recognizes the fastening position on the body where it is fastened, and the motion type of any physical exercise. For instance, there is the following described criterion that the fastening position is selected from a group consisting of a wrist position, an upper arm position and an ankle position. Most physical exercise types are respectively employed to exercise specific muscle groups. In order to avoid the occurrence of a muscle group compensation phenomenon, a physical exercise type only exercises a related muscle group of the exerciser to improve the training effect on the muscle group. Therefore, in some embodiments of the present disclosure, the fastening positions for various motion types are divided into these three types of fastening positions beforehand based on the main muscle groups that are exercised by each motion type.

In concise words, to exercise the muscle groups in the arm and the hand, the fastening position is the wrist position. To exercise the muscle groups in the chest, the back, the waist and the stomach, the fastening position is the upper arm position. To exercise the muscle groups in the leg and the foot, the fastening position is the ankle position. Larger system extensibility can be obtained through division; that is, more physical exercise types can be recognized. The recognition result of the fastening position serves as the main basis for the motion type recognition, wherein the fastening position is changeable according to the motion type (or the physical exercise type).

The second motion recognition algorithm performed in any of the motion recognition devices 20, 30 and 40 includes processing a six-axis sense signal with signal fusion, recognizing the fastening position, a periodic-motion start/termination decision, determining an effective reference signal, and recognizing the motion type. The second motion recognition algorithm is described as follows by taking the motion recognition device 20 as an example.

The sensing unit 21 includes the accelerometer 211 and the gyroscope 212, and generates the sense signal SE1 in response to the first body motion ML1 occurring at the specific position PL1 on the user's body 91, wherein the first body motion ML1 belongs to the motion segment of the first motion type HM1. The processing unit 22 receives the sense signal SE1 from the sensing unit 21, and generates the motion parameter signal structure SP1 in response to the sense signal SE1. The accelerometer 211 generates the accelerometer signal SE11 (or a first signal) which is a first three-axis sense signal; and the gyroscope 212 generates the gyroscope signal SE12 (or a second signal) which is a second three-axis sense signal. For instance, the sense signal SE1 is a six-axis sense signal, and includes the accelerometer signal SE11 and the gyroscope signal SE12; and the motion parameter signal structure SP1 includes a fusion signal SPS0 of the accelerometer signal SE11 and the gyroscope signal SE12. The fusion signal SPS0 is generated by using a signal fusion operation, and is a signal of an estimated angle SK1. The signal fusion operation includes calculating the signal of the estimated angle SK1 based on the accelerometer signal SE11 and the gyroscope signal SE12. The accelerometer signal SE11 is expressed as follows.

$$\vec{a}\, *= \vec{a}_{ideal} + \vec{a}_{noise} + \vec{a}_{bias} + \vec{a}_{gav}$$

The gyroscope signal SE12 is expressed as follows.

$$\vec{\omega}\, *= \vec{\omega}_{ideal} + \vec{\omega}_{noise} + \vec{\omega}_{bias}$$

In a first state that the motion recognition device 20 is at rest, the processing unit 22 roughly obtains an estimated pitch angle and an estimated roll angle based on the accelerometer signal SE11. The calculation method for the estimated pitch angle and the estimated roll angle is described as follows.

In this first state, the accelerometer signal SE11 is expressed by $\vec{a}\,*static = \vec{a}_{gav} + \vec{a}_{noise} + \vec{a}_{bias} = \vec{g}$. Based on the accelerometer signal SE11, an estimate of a roll angle of the motion recognition device 20 is expressed by $\varphi_{Roll} = \tan^{-1}(g_y/g_z)$. Based on the accelerometer signal SE11, an estimate of a pitch angle of the motion recognition device 20 is expressed by $\theta_{Pitch} = \tan^{-1}(g_x/\sqrt{g_y^2 + g_z^2})$.

The processing unit 22 performs a filter and calibration operation to the accelerometer signal SE11 to generate a third signal. Estimates of the roll angle and the pitch angle of the motion recognition device 20 are expressed as follows.

$$\varphi^a_{Roll} = \tan^{-1}\left\{\frac{a^*_{y,static}}{a^*_{z,static}}\right\}$$

$$\varphi^a_{Pitch} = \tan^{-1}\left\{\frac{a^*_{x,static}}{\sqrt{(a^*_{y,static})^2 + (a^*_{z,static})^2}}\right\}$$

In the first state when the motion recognition device 20 is at rest, the gyroscope signal SE12 is expressed by $\vec{\omega}\,*_{static} = \vec{\omega}_{noise} + \vec{\omega}_{bias} + \vec{\omega}_{idea}$, wherein $\vec{\omega}_{idea}$ should be 0. Then, $\vec{\omega}\,*_{static} = \vec{\omega}_{noise} + \vec{\omega}_{bias}$. Under this condition, the bias of the gyroscope 212 can be calibrated anew, thereby suppressing any error, which results from the component $\vec{\omega}_{bias}$ in the attitude algorithm.

When the motion of the motion recognition device 20 continuously changes, estimates of the roll angle and the pitch angle of the motion recognition device 20 can be calculated based on the following dynamic equation including the measured body angular velocity and the attitude angles, which includes the roll angle φ and the pitch angle θ.

$$\begin{bmatrix} \dot{\varphi}_{Roll}^{\omega} \\ \dot{\theta}_{Pitch}^{\omega} \end{bmatrix} = \begin{bmatrix} 1 & \sin(\varphi)\tan(\theta) & \cos(\varphi)\tan(\theta) \\ 0 & \cos(\varphi) & -\sin(\varphi) \end{bmatrix} \begin{bmatrix} \omega_x^* \\ \omega_y^* \\ \omega_z^* \end{bmatrix}$$

In the signal fusion operation, when the motion recognition device 20 is relatively static (i.e., $\ddot{\omega} \approx 0$, and $\dot{a} \approx 0$), the roll angle $\varphi$ and the pitch angle $\theta$ satisfy the following equations.

$$\varphi_{Roll} = \varphi_{Roll}^a; \text{ and } \theta_{Pitch} = \theta_{Pitch}^a$$

The obtained roll angle $\varphi_{Roll}$ and the obtained pitch $\theta_{Pitch}$ form the integral initial values of the mentioned dynamic equation, and are substituted into the mentioned dynamic equation to obtain the estimated roll angle $\varphi_{Roll}^\omega$ and the estimated pitch angle $\theta_{Pitch}^\omega$.

In the signal fusion operation, the processing unit 22 obtains the estimated roll angle $\varphi_{Roll}$ and the estimated pitch angle $\theta_{Pitch}$ by performing the following operation.

$$\varphi_{Roll} = \varphi_{Roll}^\omega + \alpha * Res\varphi_{Roll}$$

$$Res\varphi_{Roll} = \varphi_{Roll}^a - \varphi_{Roll}^\omega$$

$$\Rightarrow \varphi_{Roll} = \varphi_{Roll}^\omega(1-\alpha) + \alpha\varphi_{Roll}^a,$$ wherein when the motion recognition device 20 is relatively static, the value of $\alpha$ approaches 1.

On the contrary, when the motion recognition device 20 is moving, the value of $\alpha$ approaches 0. The estimated pitch angle $\theta_{Pitch}$ is expressed similar to the estimated roll angle $\varphi_{Roll}$, and is shown as follows.

$$\theta_{Pitch} = \theta_{Pitch}^\omega(1-\alpha) + \alpha\theta_{Pitch}^a$$

The motion parameter signal structure SP1 includes a plurality of motion parameter signals SP11, SP12, SP13, ... SP18 and SP19, which include the third signal $\vec{a}_{acc}^f$, the fourth signal $\vec{\omega}_{gyro}^f$, a signal of the estimated roll angle $\varphi_{Roll}$, and a signal of the estimated pitch angle $\theta_{Pitch}$. For instance, the signal of the estimated roll angle $\varphi_{Roll}$, and the signal of the estimated pitch angle $\theta_{Pitch}$ are a first fusion signal and a second fusion signal, respectively; and the signal of the estimated angle SK1 is the signal of the estimated pitch angle $\theta_{Pitch}$. As shown in FIG. 12, the user's body 91 includes the specific body portion 911, having the first body motion ML1, at the specific position PL1. For instance, the specific body portion 911 is the wrist, the upper arm or the ankle. The motion recognition device 20 further includes the push button 23, which is coupled to the processing unit 22, and serves as a motion initiation push button. In the state that the orientation KA1 is directed to the predetermined direction QH1 in relation to the gravity direction QF1, the push button 23 provides the trigger signal ST1 in response to a user button-press from the user 90, and the processing unit 22 makes the first decision on whether the processing unit 22 detects the trigger signal ST1. For instance, when the first decision is positive, the processing unit 22 obtains the specific position code CP1 based on the signal of the estimated pitch angle $\theta_{Pitch}$ and optionally the signal of the estimated roll angle $\varphi_{Roll}$. For instance, the trigger signal ST1 indicates an initiation of the first body motion ML1. The motion recognition device 20 is fastened to the specific body portion 911, which is determined according to a design arrangement, wherein the design arrangement is determined by most meeting the user 90 on the operation situation, the operation habit and the ergonomic principle.

For instance, the motion recognition device 20 has a gravitational acceleration gF, which has a gravitational acceleration direction the same as the gravity direction QF1. As shown in FIG. 12, in the state that the orientation KA1 is directed to the predetermined direction QH1 in relation to the gravity direction QF1, the push button 23 provides the trigger signal ST1 in response to the user button-press, and the processing unit 22 makes the first decision on whether the processing unit 22 detects the trigger signal ST1. When the first decision is positive, the processing unit 22 recognizes the specific position PL1 based on the estimated pitch angle $\theta_{Pitch}$ included in the motion parameter signal structure SP1 at this time. For instance, the recognition results of the specific position PL1 are classified into the following types. When the estimated pitch angle $\theta_{Pitch}$ satisfies a relationship of $-60° < \theta_{Pitch} < 60°$, the recognition result obtained by the processing unit 22 indicates that the fastening position is the wrist position and the specific position code CP1 represents the position PL5. When the estimated pitch angle $\theta_{Pitch}$ satisfies a relationship of $-120° < \theta_{Pitch} < -60°$, the recognition result obtained by the processing unit 22 indicates that the fastening position is the upper arm position and the specific position code CP1 represents the position PL6. When the estimated pitch angle $\theta_{Pitch}$ satisfies a relationship of $-60° < \theta_{Pitch} \leq 135°$, the recognition result obtained by the processing unit 22 indicates that the fastening position is the ankle position and the specific position code CP1 represents the position PL9. When finishing the recognition of the fastening position, the first stage of the motion type recognition is completed.

In some embodiments, the first motion type HM1 is one selected from a plurality of motion types HA1, HA2, ... HA6. The plurality of motion types HA1, HA2, ... HA6 are predetermined in relation to the specific position PL1, and respectively have a plurality of principal motion axis directions QA1, QA2, ... QA6 in relation to the body coordinate system UA1. The plurality of principal motion axis directions QA1, QA2, ... QA6 are detected beforehand to generate a plurality of principal motion axis direction data units DQ1, DQ2, ... DQ6 respectively corresponding to the plurality of principal motion axis directions QA1, QA2, ... QA6. The processing unit 22 obtains a recognition reference data unit DR based on the specific position code CP1. The recognition reference data unit DR is predetermined based on the plurality of principal motion axis direction data units DQ1, DQ2, ... DQ6, and includes a candidate reference signal code data unit CA and a motion type indicator data unit CH.

The candidate reference signal code data unit CA includes a first candidate reference signal code CA2, a second candidate reference signal code CA1 and a third candidate reference signal code CA3. The first, the second and the third candidate reference signal codes CA2, CA1 and CA3 respectively represent a first candidate reference signal SR2, a second candidate reference signal SR1 and a third candidate reference signal SR3, each of which is derived from the motion parameter signal structure SP1. The motion type indicator data unit CH includes a first motion type indicator, a second motion type indicator and a third motion type indicator respectively corresponding to the first, the second and the third candidate reference signal codes CA2, CA1 and CA3, wherein the first motion type indicator is a motion type indicator CH2. The motion type indicator CH2 indicates one of an invalid motion type and a second motion type HM2 included in the plurality of motion types HA1, HA2, ... HA6. The processing unit 22 determines the first, the second and the third candidate reference signals SR2, SR1 and SR3 based on the motion parameter signal structure SP1 and the first, the second and the third candidate reference signal codes CA2, CA1 and CA3.

In some embodiments, the first, the second and the third candidate reference signals SR2, SR1 and SR3 constitute a candidate reference signal combination SRG. The recognition reference data unit DR further includes a representative signal code CB1 representing a representative signal SPS1 included in the plurality of motion parameter signals SP11, SP12, SP13, . . . SP18 and SP19. The processing unit 22 determines the representative signal SPS1 based on the motion parameter signal structure SP1 and the representative signal code CB1.

For instance, the specific position code CP1 represents the position PL9 (or the ankle position). For instance, the first candidate reference signal SR2 is an acceleration differentiation signal $\dot{a}_{acc,x}$, which is derived from the acceleration signal $a_{acc,x}^{f}$ included in the motion parameter signal structure SP1. The second candidate reference signal SR1 is a sum signal ($\dot{a}_{acc,x}+\dot{a}_{acc,y}$), which is a sum of an acceleration differentiation signal $\dot{a}_{acc,x}$ and an acceleration differentiation signal $\dot{a}_{acc,y}$. The acceleration differentiation signals $\dot{a}_{acc,x}$ and $\dot{a}_{acc,y}$ are respectively derived from the acceleration signals $a_{acc,x}^{f}$ and $a_{acc,y}^{f}$ included in the motion parameter signal structure SP1. The third candidate reference signal SR3 is an angular velocity signal $\omega_{x}^{f}$ included in the motion parameter signal structure SP1. The representative signal SPS1 is the acceleration signal $a_{acc,x}^{f}$ included in the motion parameter signal structure SP1.

The processing unit 22 obtains a plurality of motion characteristic values from the motion parameter signal structure SP1 based on the first, the second and the third candidate reference signals SR2, SR1 and SR3. After the fastening position is determined, the processing unit 22 determines the candidate reference signal combination SRG based on the recognition reference data unit DR. For instance, when the fastening position is recognized as the ankle position, the processing unit 22 simultaneously triggers the first, the second and the third candidate reference signals SR2, SR1 and SR3 (such as $\dot{a}_{acc,x}$, ($\dot{a}_{acc,x}+\dot{a}_{acc,y}$) and $\omega_{x}^{f}$) to obtain the plurality of motion characteristic values. The recognition reference data unit DR is predetermined, and is employed to recognize the first motion type HM1.

For instance, the first body motion ML1 is a reciprocating motion, and includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. The processing unit 22 obtains the plurality of motion characteristic values from the motion parameter signal structure SP1 based on the first, the second and the third candidate reference signals SR2, SR1 and SR3 during the second motion cycle W2. The main motion characteristic values of the plurality of motion characteristic values include of $\bar{a}_{max}^{f}$, $\bar{a}_{min}^{f}$, $\bar{\omega}_{max}^{f}$, $\bar{\omega}_{min}^{f}$, $\varphi_{Roll,max}$, $\varphi_{Roll,min}$, $\theta_{Pitch,max}$ and $\theta_{Pitch,min}$. The plurality of motion characteristic values are expressed by motion characteristic values $DFE_{n}$, wherein n is a natural number, and is between 1 and 27.

Each of the first, the second and the third candidate reference signals SR2, SR1 and SR3 includes a first motion reference signal portion and a second motion reference signal portion respectively corresponding to the first and the second motion portions ML11 and ML12. The processing unit 22 obtains a first motion characteristic value data unit DA2, a second motion characteristic value data unit DA1 and a third motion characteristic value data unit DA3 from the motion parameter signal structure SP1 respectively based on the first, the second and the third candidate reference signals SR2, SR1 and SR3. For instance, the first candidate reference signal SR2 includes a first candidate reference signal portion SR21 and a second candidate reference signal portion SR22 respectively corresponding to the first and the second motion portions ML11 and ML12, wherein the second candidate reference signal portion SR22 is adjacent to the first candidate reference signal portion SR21.

For instance, the first motion characteristic value data unit DA2 includes a first motion characteristic value data unit portion DA21 and a second motion characteristic value data unit portion DA22 respectively corresponding to the first and the second motion portions ML11 and ML12. The processing unit 22 obtains the first motion characteristic value data unit portion DA21 from the first motion parameter signal structure portion SP5 based on the first candidate reference signal portion SR21. The processing unit 22 obtains the second motion characteristic value data unit portion DA22 from the second motion parameter signal structure portion SP6 based on the second candidate reference signal portion SR22. The processing unit 22 generates a difference data unit DC1 based on the first and the second motion characteristic value data unit portions DA21 and DA22, and makes a second decision on whether the difference data unit DC1 satisfies a first specific condition for a periodic-motion start decision. The processing unit 22 obtains a representative extreme value deviation DC11 between the first and the second motion characteristic value data unit portions DA21 and DA22 by comparing the first motion characteristic value data unit portion DA21 with the second motion characteristic value data unit portion DA22.

For instance, the first motion characteristic value data unit portion DA21 includes a first motion characteristic value data unit sub-portion DA21A corresponding to the representative signal SPS1, wherein the first motion characteristic value data unit sub-portion DA21A has a first maximum value, a first minimum value, and a first difference between the first maximum value and the first minimum value. The second motion characteristic value data unit portion DA22 includes a second motion characteristic value data unit sub-portion DA22A corresponding to the representative signal SPS1, wherein the second motion characteristic value data unit sub-portion DA22A has a second maximum value, a second minimum value, and a second difference between the second maximum value and the second minimum value. The processing unit 22 obtains a representative value difference DC12 from the first and the second differences. The difference data unit DC1 includes the representative extreme value deviation DC11 and the representative value difference DC12. The first specific condition includes a first sub-condition and a second sub-condition. The first sub-condition is that the representative extreme value deviation DC11 falls within a first predetermined value range. The second sub-condition is that the representative value difference DC12 falls within a second predetermined value range.

For instance, the second decision includes a first sub-decision and a second sub-decision. The first sub-decision is made on whether the representative extreme value deviation DC11 falls within the first predetermined value range, or on whether each of the corresponding characteristic value errors or deviations between the first and the second motion characteristic value data unit portions DA21 and DA22 is less than a threshold value $\delta_{n}$. When the first sub-decision is positive, the second sub-decision is made on whether the representative value difference DC12 falls within the second predetermined value range. When the second sub-decision is positive, the second decision is positive, and the processing unit 22 recognizes the effective reference signal SRP as the first candidate reference signal SR2, determines that the first body motion ML1 satisfies a predetermined periodic-motion start condition, and based on the motion type indicator CH2, makes a third decision on whether the motion type indicator CH2 indicates one selected from the plurality of motion types HA1, HA2, . . . HA6. When the third decision is positive, the processing unit 22, based on the motion type indicator CH2, recognizes the first motion type HM1 as the second motion type HM2, and obtains a motion type code CT1 representing the first motion type HM1. When the second sub-decision is negative, the processing unit 22 determines that the first body motion ML1 satisfies a predetermined periodic-motion termination condition, or determines that the first body motion ML1 does not satisfy the predetermined periodic-motion start condition.

In some embodiments, the specific position PL1 is configured to be the ankle position; and the plurality of motion types HA1, HA2, . . . HA6 includes a hip adduction, a side-leg lift and a knee lift. When the first body motion ML1 belonging to the hip adduction occurs at the ankle position, the processing unit 22 recognizes the effective reference signal SRP as the third candidate reference signal SR3 (or the angular velocity signal $\omega_x^f$) based on the second decision. When the first body motion ML1 belonging to one of the side-leg lift and the knee lift occurs at the ankle position, the processing unit 22 recognizes the effective reference signal SRP as the first candidate reference signal SR2 (or the acceleration differentiation signal $\dot{a}_{acc,x}$) based on the second decision.

For instance, when the first candidate reference signal SR2 (or the acceleration differentiation signal $\dot{a}_{acc,x}$) is employed to obtain the first motion characteristic value data unit DA2 and the first sub-decision is positive and the representative value difference DC12 is equal to or greater than 2500, the third decision is made to be negative and the first motion type HM1 is recognized as one of the side-leg lift and the knee lift based on the first characteristic function code data unit F1. Otherwise, when the first candidate reference signal SR2 is employed to obtain the first motion characteristic value data unit DA2 and the first sub-decision is positive and the representative value difference DC12 is less than 2500, the second decision is made to be negative. For instance, the third motion type indicator indicates the hip adduction. When the third candidate reference signal SR3 (or the angular velocity signal $\omega_x^f$) is employed to obtain the third motion characteristic value data unit DA3 and the representative value difference DC12 is less than 2500, the third decision is made to be positive and the first motion type HM1 is recognized as the hip adduction.

Otherwise, when the third candidate reference signal SR3 is employed to obtain the third motion characteristic value data unit DA3 and the representative value difference DC12 is equal to or greater than 2500, the second decision is made to be negative. When a specific motion characteristic value data unit obtained based on a specific candidate reference signal satisfies a predetermined condition for the periodic-motion start decision, the following characteristic function is performed based on the specific motion characteristic value data unit. At the same time, the processing unit 22 recognizes the effective reference signal SRP as the specific candidate reference signal, and stops triggering the other candidate reference signals.

In some embodiments, the processing unit 22 provides beforehand a first characteristic function code data unit F1, which is associated with the first candidate reference signal code CA2 and a first plurality of recognition value domains DU1, DU2 and DV1. The first characteristic function code data unit F1 is employed to indicate one of the first plurality of recognition value domains DU1, DU2 and DV1. The first plurality of recognition value domains DU1, DU2 and DV1 include a first recognition value domain DU1, a second recognition value domain DU2 adjacent to the first recognition value domain DU1, and a first confidence value domain DV1 between the first and the second recognition value domains DU1 and DU2. For instance, the first confidence value domain DV1 is optional. The first and the second recognition value domains DU1 and DU2 respectively indicate a third motion type H1 and a fourth motion type H2, each of which is included in the plurality of motion types HA1, HA2, . . . HA6.

When the third decision is negative, the processing unit 22 performs a first calculation to generate a first recognition value DH1 based on the first characteristic function code data unit F1 and the second motion characteristic value data unit portion DA22, and makes a fourth decision on whether the first recognition value DH1 belongs to one of the first and the second recognition value domains DU1 and DU2. When the fourth decision is positive, the processing unit 22 determines an effective recognition value domain DUA in the first and the second recognition value domains DU1 and DU2 that the first recognition value DH1 belongs to, recognizes the first motion type HM1 as an effective motion type indicated by the effective recognition value domain DUA, and obtains the motion type code CT1 corresponding to the effective recognition value domain DUA. The processing unit 22 generates a motion measurement information DM1 associated with the first body motion ML1 based on the motion type code CT1.

In some embodiments, the processing unit 22 further provides beforehand a second characteristic function code data unit F2, which is associated with the first candidate reference signal code CA2, a third recognition value domain DU3, and a fourth recognition value domain DU4 adjacent to the third recognition value domain DU3. When the fourth decision is negative, the processing unit 22 performs a second calculation to generate a second recognition value DH2 based on the second characteristic function code data unit F2 and the second motion characteristic value data unit portion DA22, decides whether the second recognition value DH2 belongs to one of the third and the fourth recognition value domains DU3 and DU4, and thereby recognizes the first motion type HM1.

In some embodiments, the processing unit 22 provides a set of characteristic function code data units F1, F2, and so forth beforehand respectively representing a set of motion type cut functions $P_{1-K}$, which is established by calculating large volumes of data, which are qualified to satisfy the periodic-motion start conditions of the plurality of motion types HA1, HA2, . . . HA6. For instance, the processing unit 22 performs a calculation to effectively recognize the first motion type HM1 based on at least one selected from the set of characteristic function code data units F11, F12, and so forth and the motion characteristic values $DFE_n$ (including the second motion characteristic value data unit portion DA22). The set of motion type cut functions $P_{1-K}$ has a set of cut planes and a hierarchy number K, wherein K is a natural number. When K is greater than 1, the set of motion type cut functions is arranged according to an order, and are at least partially employed to recognize the first motion type HM1. For instance, it is sufficient for the processing unit 22 to recognize the first motion type HM1 as one of the side-leg lift and the knee lift by employing the motion type cut function $P_1$.

For instance, the set of motion type cut functions $P_{1 \sim K}$ is expressed as follows.

$P_i = F(DFE_{1 \sim n}) \pm \sigma$, $i = 1 \sim K$, wherein $\sigma$ represents a threshold distance of a confidence value domain. For instance, the confidence value distance $\sigma 1$ of the first confidence value domain DV1 is equal to $2\sigma$.

For instance, the motion type cut function $P_1$ is expressed as follows.

$$P_1 = \{abs(a_{z,Max} + 6000)/1000\} \cdot \{abs(a_{z,Min} + 6000)/1000\} \cdot \{abs(\theta_{Pitch,max} + 90)/100\} \cdot \{abs(\theta_{Pitch,min} + 180)/100\} \pm 20$$

For instance, the processing unit 22 performs the first calculation to generate a calculation result value (or the first recognition value DH1) by substituting the motion characteristic values $DFE_n$ into the motion type cut function $P_1$, wherein the motion type cut function $P_1$ is expressed by a relationship among the motion characteristic values $DFE_n$. When the calculation result value is equal to or less than 130, the processing unit 22 recognizes the first motion type HM1 as the side-leg lift. When the calculation result value is greater than 130, the processing unit 22 recognizes the first motion type HM1 as the knee lift. For instance, the first and the second characteristic function code data units F1 and F2 respectively represent the motion type cut functions $P_1$ and $P_2$.

In some embodiments, the processing unit 22 provides beforehand a plurality of characteristic value range tables respectively corresponding to the plurality of motion types HA1, HA2, ... HA6, wherein the plurality of characteristic value range tables include a specific characteristic value range table corresponding to the first motion type HM1. Each of the motion characteristic values $DFE_n$ is associated with a corresponding characteristic value range in the specific characteristic value range table. When the recognition of the first motion type HM1 succeeds, the processing unit 22 makes a fifth decision on whether each of the motion characteristic values $DFE_n$ falls within the respective corresponding characteristic value range. When the fifth decision is positive, the processing unit 22 determines that the recognition of the first motion type HM1 is successful. When the fifth decision is negative, the processing unit 22 determines that the recognition of the first motion type HM1 fails, and triggers the candidate reference signal combination SRG anew.

Figure 16:
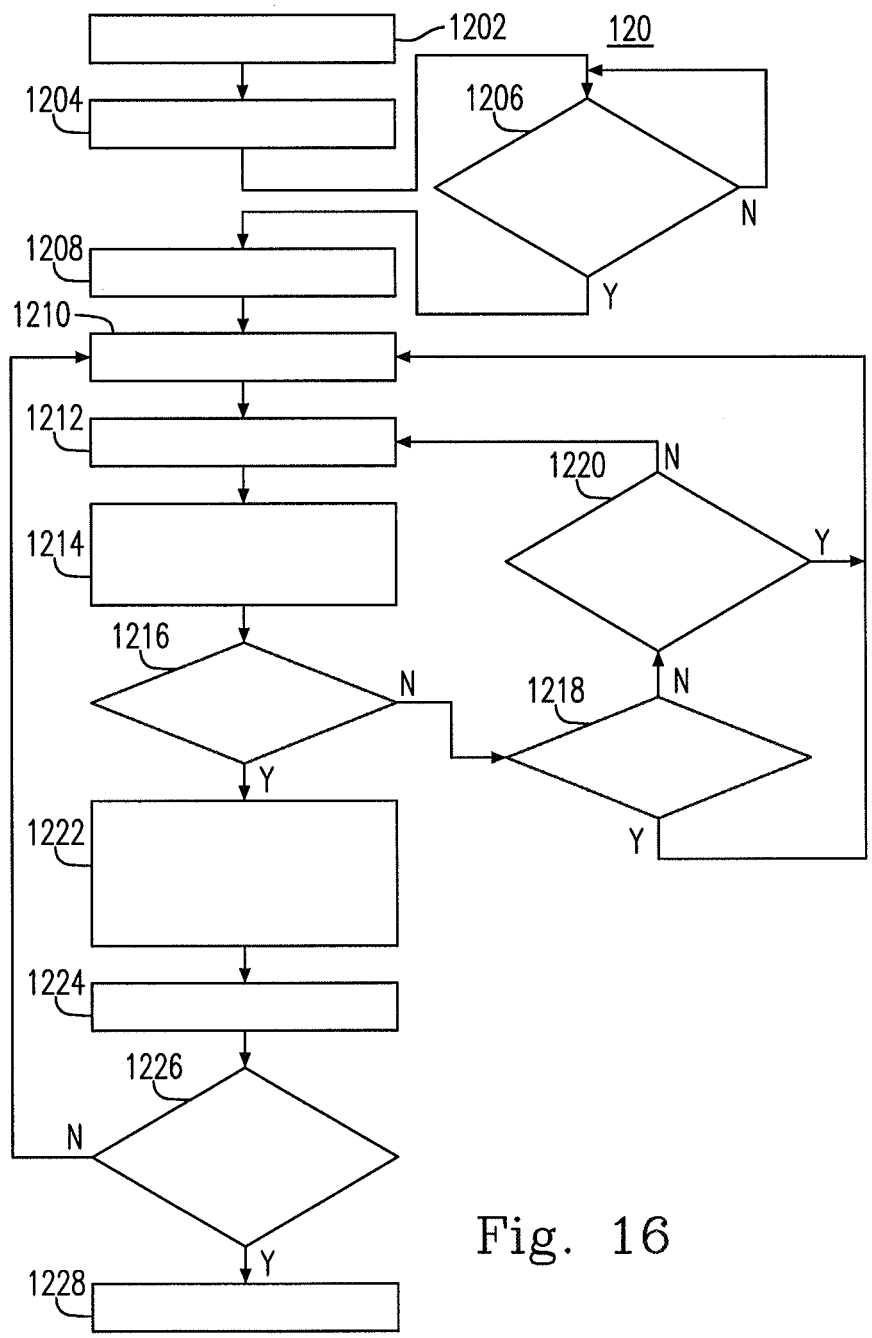
FIG. 16 is a schematic diagram showing a flow of a second motion type recognition algorithm according to various embodiments of the present disclosure.

Please refer to FIG. 16, which is a schematic diagram showing a flow of a second motion type recognition algorithm 120 according to various embodiments of the present disclosure. In step 1202, the sensing unit 21 generates a sense signal SE1 in response to a first body motion ML1 occurring at a specific position PL1 on a user's body 91. The first body motion ML1 belongs to a first motion type HM1; and the sense signal is generated in relation to a body coordinate system UA1 of the sensing unit 21.

In step 1204, the processing unit 22 or the converting unit 411 processes the sense signal SE1 to generate a motion parameter signal structure SP1, wherein the sense signal SE1 includes an accelerometer signal SE11 and a gyroscope signal SE12, and the motion parameter signal structure SP1 can include a fusion signal SPS0 of the accelerometer signal SE11 and the gyroscope signal SE12.

In step 1206, the processing unit 22 makes a first decision on whether the processing unit 22 detects a trigger signal ST1. When the first decision is negative, the step after step 1106 returns to step 1206. When the first decision is positive, the step after step 1106 is step 1208.

In step 1208, the processing unit 22 generates a specific position code CP1 representing the specific position PL1 based on the motion parameter signal structure SP1. The user's body 91 wears the motion recognition device 20 at the specific position PL1, wherein the motion recognition device 20 includes the body coordinate system UA1, the sensing unit 21 and the processing unit 22.

In step 1210, the processing unit 22 obtains a recognition reference data unit DR based on the specific position code CP1. The recognition reference data unit DR is predetermined based on the body coordinate system UA1 and a principal motion axis direction of the first motion type HM1, and includes a candidate reference signal code data unit CA including a plurality of candidate reference signal codes (such as a first candidate reference signal code CA2, a second candidate reference signal code CA1 and a third candidate reference signal code CA3). The plurality of candidate reference signal codes (such as the first, the second and the third candidate reference signal codes CA2, CA1 and CA3) respectively represents a plurality of candidate reference signals (such as a first candidate reference signal SR2, a second candidate reference signal SR1 and a third candidate reference signal SR3), each of which is derived from the motion parameter signal structure SP1.

In step 1210, the processing unit 22 determines the plurality of candidate reference signals (such as the first, the second and the third candidate reference signals SR2, SR1 and SR3) based on the motion parameter signal structure SP1 and the plurality of candidate reference signal codes (such as the first, the second and the third candidate reference signal codes CA2, CA1 and CA3).

In step 1212, the processing unit 22 obtains a plurality of motion characteristic value data units (such as a first motion characteristic value data unit DA2, a second motion characteristic value data unit DA1 and a third motion characteristic value data unit DA3) from the motion parameter signal structure SP1 based on the plurality of candidate reference signals (such as the first, the second and the third candidate reference signals SR2, SR1 and SR3) respectively corresponding to the plurality of motion characteristic value data units. The first body motion ML1 includes a first motion portion ML11 and a second motion portion ML12 adjacent to the first motion portion ML11. The first and the second motion portions ML11 and ML12 respectively form a first motion cycle W1 and a second motion cycle W2 adjacent to the first motion cycle W1. Each of the plurality of motion characteristic value data units (such as the first, the second and the third motion characteristic value data units DA2, DA1 and DA3) includes a first motion characteristic value data unit portion and a second motion characteristic value data unit portion respectively corresponding to the first and the second motion portions ML11 and ML12.

In step 1214, the processing unit 22 generates a plurality of difference data units respectively corresponding to the plurality of motion characteristic value data units (such as the first, the second and the third motion characteristic value data units DA2, DA1 and DA3) based on the respective first and the respective second motion characteristic value data unit portions, and employs the plurality of difference data units to decide whether the first body motion ML1 effectively terminates or starts. The plurality of difference data units respectively includes a plurality of representative extreme value deviations, each of which is generated by comparing the respective first motion characteristic value data unit portion with the respective second motion characteristic value data unit portion.

In step 1216, the processing unit 22 makes a second decision on whether the plurality of difference data units includes a first difference data unit best satisfying a first specific condition for a periodic-motion start decision. When the second decision is negative, the step after step 1216 is step 1218. When the second decision is positive, the step after step 1216 is step 1222.

In step 1218, the processing unit 22 makes a third decision on whether any of plurality of difference data units satisfies a second specific condition for a motion termination decision. When the third decision is negative, the step after step 1218 is step 1220. When the third decision is positive, the step after step 1218 returns to step 1210.

In step 1220, the processing unit 22 makes a fourth decision on whether a current negative decision number of the third decision reaches a predetermined threshold number. When the fourth decision is negative, the step after step 1220 returns to step 1212. When the fourth decision is positive, the step after step 1220 returns to step 1210.

In step 1222, the processing unit 22 recognizes the effective reference signal SRP as a fourth candidate reference signal corresponding to the first difference data unit, and determines that the first body motion ML1 satisfies a predetermined periodic-motion start condition, wherein the fourth candidate reference signal is included in the plurality of candidate reference signals.

In step 1224, the processing unit 22 performs a calculation to recognize the first motion type HM1 based on at least a first characteristic function code data unit F1 and a fourth motion characteristic value data unit corresponding to the first difference data unit, wherein the fourth motion characteristic value data unit is included in the plurality of motion characteristic value data units.

In step 1226, the processing unit 22 makes a fifth decision on whether it is successful to recognize the first motion type HM1 by performing the calculation. When the fifth decision is negative, the step after step 1226 returns to step 1210. When the fifth decision is positive, the step after step 1226 is step 1228.

In step 1228, the processing unit 22 obtains a motion type code CT1 representing the first motion type HM1, and generates a motion measurement information DM1 associated with the first body motion ML1 based on the motion type code CT1.

Figure 17A:
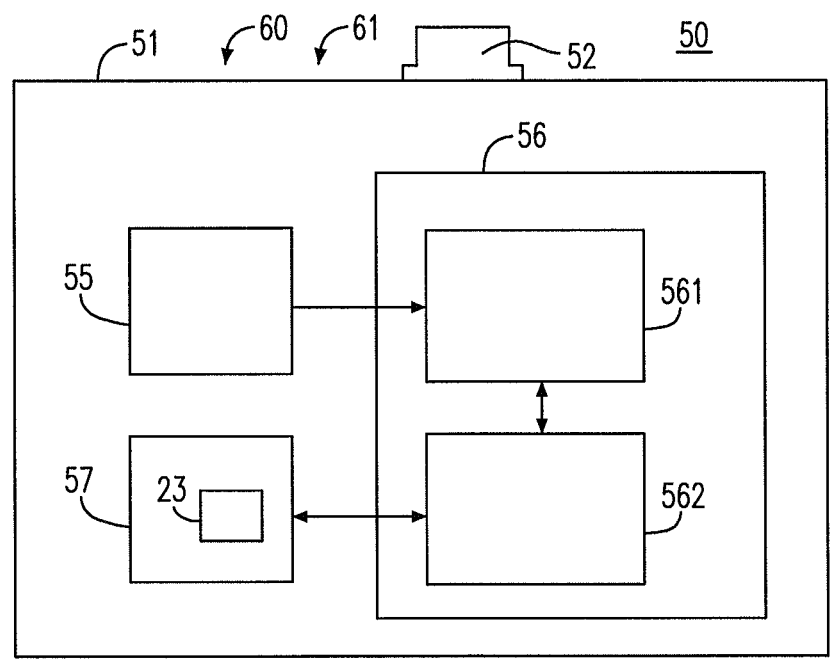
FIG. 17A is a structural diagram showing a motion recognition device according to various embodiments of the present disclosure.
Figure 17B:
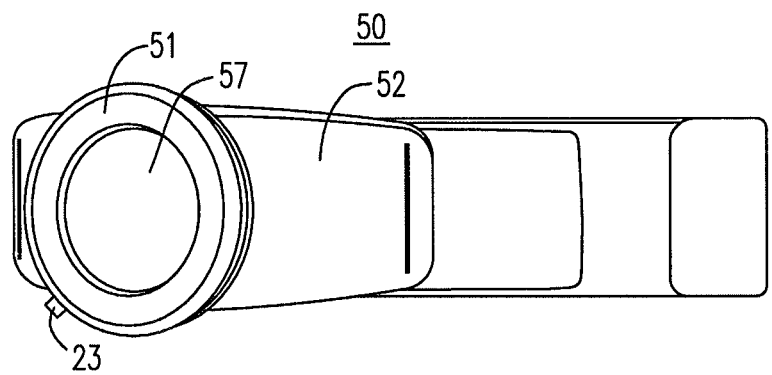
FIG. 17B is a profile diagram showing the motion recognition device illustrated in FIG. 17A.

Please refer to FIG. 17A and FIG. 17B. FIG. 17A is a structural diagram showing a motion recognition device 50 according to various embodiments of the present disclosure. FIG. 17B is a profile diagram showing the motion recognition device 50 illustrated in FIG. 17A. The motion recognition device 50 is a wearable motion-sensing device, and includes an operating unit 51 and a coupling unit 52 coupled to the operating unit 51. For instance, the coupling unit 52 is a fastening component. The operating unit 51 includes a motion-sensing unit 55, a processing unit 56 and a man-machine interface unit 57. The processing unit 56 includes a motion recognition module 561 and a signal processing module 562, and is coupled to the motion-sensing unit 55 and the man-machine interface unit 57, wherein the signal processing module 562 is coupled to the motion recognition module 561 and the man-machine interface unit 57.

In some embodiments, the motion-sensing unit 55 is configured to include at least a motion sensor such as an accelerometer, a gyroscope or a magnetometer. The coupling unit 52 is employed to install the motion-sensing unit 55, and is fastened to a body portion of a physical exerciser, so that the motion-sensing unit 55 is suitable to sense a motion. The motion recognition module 561 includes at least one selected from a group consisting of a motion recognition function code data unit, a motion recognition specification, a recognition parameter, a recognition reference value, a threshold value, a relevant algorithm, and so forth, wherein the motion recognition function code data unit represents a motion recognition function. The signal processing module 562 is employed to receive an input from the physical exerciser, outputs, displays or accesses relevant physical exercise data. For instance, the signal processing module 562 is employed to display or access a sensed motion status, a cycle number of the physical exercise, an energy consumption, and so forth. The man-machine interface unit 57 can communicate with an intelligent mobile phone, and is configured to have a wireless communication device, such as having a built-in Bluetooth® function, is coupled to the motion-sensing unit 55 to transmit data, and is coupled to the signal processing module 562 to receive, process, calculate or store data, or the like. For instance, the man-machine interface unit 57 includes a push button 23 coupled to the signal processing module 562. The motion-sensing unit 55 and the processing unit 56 are respectively similar to the sensing unit 21 and the processing unit 22 illustrated in FIG. 1. In addition, the motion recognition device 50 further operates based on the functions of the motion recognition device 20 illustrated in FIG. 1.

In some embodiments disclosed according to the illustrations in FIGS. 17A and 17B, a motion recognition device 60 is a wearable device, is configured to measure a body motion, and includes a motion-sensing unit 55, a coupling unit 52, a motion recognition module 561, a signal processing module 562 and a man-machine interface unit 57. The motion-sensing unit 55 includes at least an accelerometer, a gyroscope or a magnetometer, and senses the body motion to generate a motion sense signal. The coupling unit 52 includes a joining structure and a fastening device coupled to the joining structure. The motion-sensing unit 55 is fixed to the joining structure. The fastening device is fastened to a body portion of a user. The motion recognition module 561 is electrically connected to the motion-sensing unit 55, has a signal recognition function code data unit, processes the motion sense signal by employing the signal recognition function code data unit, and thereby determines that the body motion meets a specific motion specification, wherein the signal recognition function code data unit represents a signal recognition function. The signal processing module 562 is electrically connected to the motion-sensing unit 55, has a signal processing function code data unit, recognizes the body motion, meeting the first specific motion specification, as a first specific motion by employing the signal processing function code data unit, and generates a motion information associated with the body motion, wherein the motion information forms a record, and the signal processing function code data unit represents a signal processing function. The man-machine interface unit 57 is electrically connected to the signal processing module 562, and outputs the motion information or receives a specification data associated with a second specific motion.

In some embodiments disclosed according to the illustrations in FIGS. 17A and 17B, a measurement method for measuring a physical exercise is disclosed. The method includes the following steps. A body motion occurring at a specific position on a user is sensed to generate a motion sense signal. The motion sense signal is processed by employing a signal recognition function code data unit, so that it is determined that the body motion meets a specific motion specification. By employing a signal processing function code data unit, the body motion, meeting the first specific motion specification, is recognized as a first specific motion, and a motion information associated with the body motion is generated, wherein the motion information forms a record. The motion information is output, or a specification data associated with a second specific motion is received.

In some embodiments disclosed according to the illustrations in FIGS. 17A and 17B, a motion recognition device 61 is a wearable device, is configured to measure a body motion, and includes a motion-sensing unit 55, a coupling unit 52, a motion recognition module 561, a signal processing module 562 and a man-machine interface unit 57. The motion-sensing unit 55 includes at least an accelerometer, a gyroscope or a magnetometer, and senses the body motion to generate a motion sense signal. The coupling unit 52 includes a joining structure and a fastening device coupled to the joining structure. The motion-sensing unit 55 is fixed to the joining structure. The fastening device is fastened to a body portion of a user. The motion recognition module 561 is electrically connected to the motion-sensing unit 55, has a signal recognition function code data unit, processes the motion sense signal by employing the signal recognition function code data unit, and thereby determines that the motion-sensing unit 55 is fastened at a specific position on the user, wherein the signal recognition function code data unit represents a signal recognition function. The signal processing module 562 is electrically connected to the motion-sensing unit 55, has a signal processing function code data unit, recognizes the body motion, meeting the first specific motion specification, as a first specific motion by employing the signal processing function code data unit, and generates a motion information associated with the body motion, wherein the motion information forms a record, and the signal processing function code data unit represents a signal processing function. The man-machine interface unit 57 is electrically connected to the signal processing module 562, and outputs the motion information or receives a specification data associated with a second specific motion.

In some embodiments disclosed according to the illustrations in FIGS. 17A and 17B, a measurement method for measuring a physical exercise is disclosed. The method includes the following steps. A body motion occurring at a specific position on a user is sensed to generate a motion sense signal. The motion sense signal is processed by employing a signal recognition function code data unit, so that the specific position where a motion-sensing unit is fastened is recognized. By employing a signal processing function code data unit, the body motion, meeting the first specific motion specification, is recognized as a first specific motion, and a motion information associated with the body motion is generated, wherein the motion information forms a record. The motion information is output, or a specification data associated with a second specific motion is received.

Figure 18:
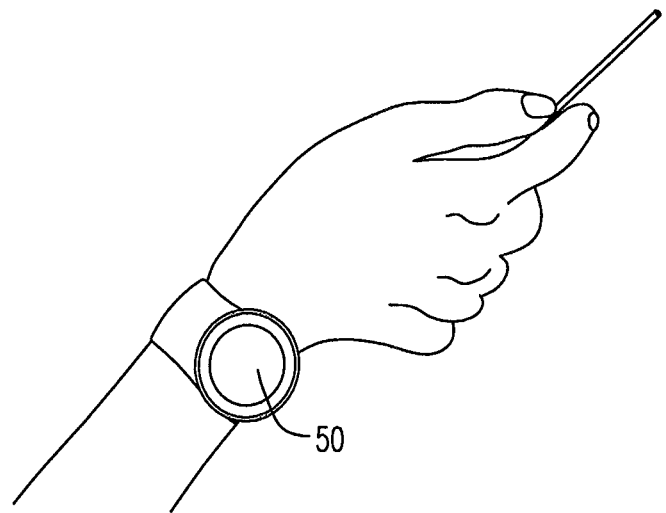
FIG. 18 is a schematic diagram showing the motion recognition device which is illustrated in FIG. 17B and is fastened to a wrist.
Figure 19:
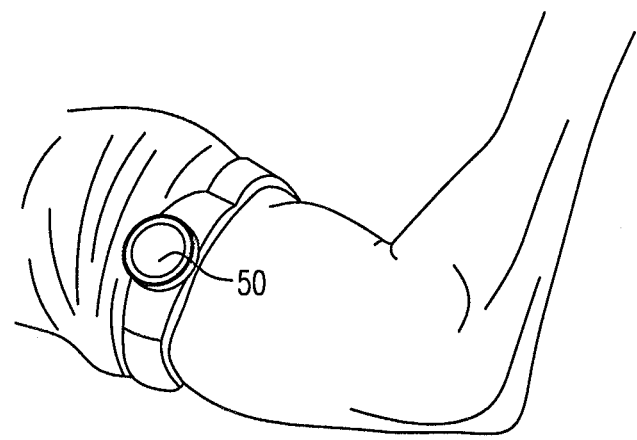
FIG. 19 is a schematic diagram showing the motion recognition device which is illustrated in FIG. 17B and is fastened to an upper arm.

Please refer to FIG. 18, which is a schematic diagram showing the motion recognition device 50 which is illustrated in FIG. 17B and is fastened to a wrist. Please refer to FIG. 19, which is a schematic diagram showing the motion recognition device 50 which is illustrated in FIG. 17B and is fastened to an upper arm.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A motion recognition device, comprising:
a sensing unit generating a sense signal in response to a first body motion occurring at a specific position out of a plurality of different positions on a user's body, wherein the sense signal includes a first sense signal portion and a second sense signal portion different from the first sense signal portion, and the first body motion belongs to a motion segment of a first motion type; and
a processing unit electrically connected to the sensing unit and processing the sense signal to generate a motion parameter signal structure including a fusion signal of the first and the second sense signal portions, and recognizing the specific position on the user's body to determine an effective reference signal for recognition of the first motion type based on the motion parameter signal structure, wherein the processing unit generates a specific position code representing the specific position based on the motion parameter signal structure, and thereby recognizes the specific position, wherein:
the specific position is selected from the plurality of different positions on the user's body;
the motion recognition device is further configured to have an orientation, a gravity direction and a body coordinate system used to determine the orientation, and fastened at the specific position;
the sense signal is generated in relation to the body coordinate system;
in a state that the orientation is directed to a predetermined direction in relation to the gravity direction, the processing unit generates the specific position code representing the specific position based on the motion parameter signal structure, and thereby recognizes the specific position;
the predetermined direction is determined based on the specific position;
the predetermined direction and the gravity direction have a first angle therebetween;
the fusion signal is a signal of an estimated angle associated with the first angle;
in this state, the processing unit makes a first decision on whether the processing unit detects a trigger signal; and
when the first decision is positive, the processing unit generates the specific position code based on the estimated angle.

2. The motion recognition device according to claim 1, wherein:
the sensing unit comprises:
an accelerometer providing an accelerometer signal to the processing unit, wherein the accelerometer signal is the first sense signal portion; and
a gyroscope providing a gyroscope signal to the processing unit, wherein the gyroscope signal is the second sense signal portion;
the first motion type is one selected from a plurality of motion types;
the plurality of motion types are predetermined in relation to the specific position, and respectively have a plurality of principal motion axis directions in relation to the body coordinate system, wherein the plurality of principal motion axis directions are detected beforehand to generate a plurality of principal motion axis direction data units respectively corresponding to the plurality of principal motion axis directions;

the processing unit obtains a recognition reference data unit based on the specific position code, wherein:

the recognition reference data unit is predetermined based on the plurality of principal motion axis direction data units, and includes a candidate reference signal code data unit and a motion type indicator data unit;

the candidate reference signal code data unit includes a first candidate reference signal code;

the first candidate reference signal code represents a first candidate reference signal derived from the motion parameter signal structure;

the motion type indicator data unit includes a motion type indicator corresponding to the first candidate reference signal code; and the motion type indicator indicates one of an invalid motion type and a second motion type included in the plurality of motion types; and the processing unit determines the first candidate reference signal based on the motion parameter signal structure and the first candidate reference signal code.

3. The motion recognition device according to claim 2, wherein:

the first body motion includes a first motion portion and a second motion portion adjacent to the first motion portion;

the first and the second motion portions respectively form a first motion cycle and a second motion cycle adjacent to the first motion cycle;

the motion parameter signal structure includes a first motion parameter signal structure portion and a second motion parameter signal structure portion respectively corresponding to the first and the second motion portions;

the first candidate reference signal includes a first candidate reference signal portion and a second candidate reference signal portion respectively corresponding to the first and the second motion portions; and the processing unit obtains a first motion characteristic value data unit from the motion parameter signal structure based on the first candidate reference signal, wherein:

the first motion characteristic value data unit includes a first motion characteristic value data unit portion and a second motion characteristic value data unit portion respectively corresponding to the first and the second motion portions;

the processing unit obtains the first motion characteristic value data unit portion from the first motion parameter signal structure portion based on the first candidate reference signal portion; and the processing unit obtains the second motion characteristic value data unit portion from the second motion parameter signal structure portion based on the second candidate reference signal portion.

4. The motion recognition device according to claim 3, wherein:

the processing unit generates a difference data unit based on the first and the second motion characteristic value data unit portions, and makes a first decision on whether the difference data unit satisfies a first specific condition for a periodic-motion start decision;

when the first decision is positive, the processing unit recognizes the effective reference signal as the first candidate reference signal, determines that the first body motion satisfies a predetermined periodic-motion start condition, and makes a second decision on whether the motion type indicator indicates one selected from the plurality of motion types based on the motion type indicator;

when the second decision is positive, the processing unit recognizes the first motion type as the second motion type based on the motion type indicator, and obtains a motion type code representing the first motion type;

the motion parameter signal structure includes a plurality of motion parameter signals;

the recognition reference data unit further includes a representative signal code representing a representative signal included in the plurality of motion parameter signals;

the processing unit determines the representative signal based on the motion parameter signal structure and the representative signal code;

the processing unit obtains a representative extreme value deviation between the first and the second motion characteristic value data unit portions by comparing the first motion characteristic value data unit portion with the second motion characteristic value data unit portion;

the first motion characteristic value data unit portion includes a first motion characteristic value data unit sub-portion corresponding to the representative signal, wherein the first motion characteristic value data unit sub-portion has a first maximum value, a first minimum value, and a first difference between the first maximum value and the first minimum value;

the second motion characteristic value data unit portion includes a second motion characteristic value data unit sub-portion corresponding to the representative signal, wherein the second motion characteristic value data unit sub-portion has a second maximum value, a second minimum value, and a second difference between the second maximum value and the second minimum value;

the processing unit obtains a representative value difference from the first and the second differences;

the difference data unit includes the representative extreme value deviation and the representative value difference;

the first specific condition includes a first sub-condition and a second sub-condition;

the first sub-condition is that the representative extreme value deviation falls within a first predetermined value range; and the second sub-condition is that the representative value difference falls within a second predetermined value range.

5. The motion recognition device according to claim 4, wherein:

the second motion portion is later than the first motion portion;

the second motion characteristic value data unit portion includes a plurality of specific motion characteristic values;

the processing unit provides beforehand a first characteristic function code data unit associated with the first candidate reference signal code and a first plurality of recognition value domains, wherein:

the first characteristic function code data unit is employed to indicate one of the first plurality of recognition value domains including a first recognition value domain, a second recognition value domain adjacent to the first recognition value domain, and a first confidence value domain between the first and the second recognition value domains; and the first and the second recognition value domains respectively indicate a third motion type and a fourth motion type, each of which is included in the plurality of motion types;

the recognition device establishes the first characteristic function code data unit beforehand by sensing a plurality of body motions occurring at the specific position, wherein the plurality of body motions are divided into a plurality of motion groups respectively belonging to the plurality of motion types;

the first characteristic function code data unit represents a motion type cut function employed to indicate the one of the first plurality of recognition value domains, and is expressed based on a relationship among the plurality of specific motion characteristic values;

when the second decision is negative, the processing unit performs a first calculation to generate a first recognition value based on the first characteristic function code data unit and the second motion characteristic value data unit portion, and makes a third decision on whether the first recognition value belongs to one of the first and the second recognition value domains;

when the third decision is positive, the processing unit determines an effective recognition value domain in the first and the second recognition value domains that the first recognition value belongs to, recognizes the first motion type as an effective motion type indicated by the effective recognition value domain, and obtains the motion type code corresponding to the effective recognition value domain; and the processing unit generates a motion measurement information associated with the first body motion based on the motion type code.

6. The motion recognition device according to claim 5, wherein:

the processing unit further provides beforehand a second characteristic function code data unit associated with the first candidate reference signal code and a second plurality of recognition value domains, wherein:

the second characteristic function code data unit is different from the first characteristic function code data unit, and is employed to indicate one of the second plurality of recognition value domains including a third recognition value domain, a fourth recognition value domain adjacent to the third recognition value domain, and a second confidence value domain between the third and the fourth recognition value domains; and the third and the fourth recognition value domains respectively indicate a fifth motion type and a sixth motion type, each of which is included in the plurality of motion types;

in a second specific condition, one of the third and the fourth recognition value domains at least partially overlaps with one of the first and the second recognition value domains; and when the third decision is negative, the processing unit performs a second calculation to generate a second recognition value based on the second characteristic function code data unit and the second motion characteristic value data unit portion, and decides whether the second recognition value belongs to one of the third and the fourth recognition value domains, and thereby recognizes the first motion type.

7. The motion recognition device according to claim 3, wherein:

the candidate reference signal code data unit further includes at least a second candidate reference signal code representing at least a second candidate reference signal, wherein:

the second candidate reference signal code represents the second candidate reference signal derived from the motion parameter signal structure; and the first candidate reference signal and the at least a second candidate reference signal constitute a candidate reference signal combination;

the processing unit determines the at least a second candidate reference signal based on the motion parameter signal structure and the at least a second candidate reference signal code, and obtains at least a second motion characteristic value data unit from the motion parameter signal structure based on the at least a second candidate reference signal, wherein the at least a second motion characteristic value data unit corresponds to the at least a second candidate reference signal; and when the processing unit processes the first motion characteristic value data unit, the processing unit processes the at least a second motion characteristic value data unit to decide whether the candidate reference signal combination includes the effective reference signal.

8. A motion recognition device, comprising:

a signal generating unit generating a motion parameter signal structure including a fusion signal in response to a body motion occurring at a specific position out of a plurality of different positions on a user's body, wherein the body motion belongs to a first motion type; and a processing unit electrically connected to the signal generating unit and recognizing the specific position on the user's body to determine an effective reference signal for recognition of the first motion type based on the motion parameter signal structure, wherein the processing unit generates a specific position code representing the specific position based on the motion parameter signal structure, and thereby recognizes the specific position, wherein:

the specific position is selected from the plurality of different positions on the user's body;

the motion recognition device is further configured to have an orientation, a gravity direction and a body coordinate system used to determine the orientation, and fastened at the specific position;

in a state that the orientation is directed to a predetermined direction in relation to the gravity direction, the processing unit generates the specific position code representing the specific position based on the motion parameter signal structure, and thereby recognizes the specific position;

the predetermined direction is determined based on the specific position;

the predetermined direction and the gravity direction have a first angle therebetween;

the fusion signal is a signal of an estimated angle associated with the first angle;

in this state, the processing unit makes a first decision on whether the processing unit detects a trigger signal; and when the first decision is positive, the processing unit generates the specific position code based on the estimated angle.

9. The motion recognition device according to claim 8, wherein:
the specific position is selected from a plurality of different positions on the user's body;
the signal generating unit comprises a sensing unit and a converting unit coupled to the sensing unit;
the sensing unit generates a sense signal in response to the body motion, and comprises;
an accelerometer providing an accelerometer signal to the processing unit; and
a gyroscope providing a gyroscope signal to the processing unit;
the converting unit generates the motion parameter signal structure in response to the sense signal, wherein the motion parameter signal structure includes a fusion signal of the accelerometer signal and the gyroscope signal;
the processing unit is coupled to the signal generating unit;
the first motion type is one selected from a plurality of motion types;
the plurality of motion types are predetermined in relation to the specific position, and respectively have a plurality of principal motion axis directions in relation to the body coordinate system, wherein the plurality of principal motion axis directions are detected beforehand to generate a plurality of principal motion axis direction data units respectively corresponding to the plurality of principal motion axis directions;
the motion parameter signal structure is generated in relation to the body coordinate system;
the processing unit obtains a recognition reference data unit based on the specific position code, wherein:
the recognition reference data unit is predetermined based on the plurality of principal motion axis direction data units, and includes a candidate reference signal code, and a motion type indicator corresponding to the candidate reference signal code;
the candidate reference signal code represents a candidate reference signal derived from the motion parameter signal structure; and
the motion type indicator indicates one of an invalid motion type and a second motion type included in the plurality of motion types; and
the processing unit determines the candidate reference signal based on the motion parameter signal structure and the candidate reference signal code.

10. The motion recognition device according to claim 9, wherein:
the body motion includes a first motion portion and a second motion portion adjacent to the first motion portion;
the first and the second motion portions respectively form a first motion cycle and a second motion cycle adjacent to the first motion cycle;
the processing unit obtains a motion characteristic value data unit from the motion parameter signal structure based on the candidate reference signal, wherein the motion characteristic value data unit includes a first motion characteristic value data unit portion and a second motion characteristic value data unit portion respectively corresponding to the first and the second motion portions;
the processing unit generates a difference data unit based on the first and the second motion characteristic value data unit portions;
the processing unit makes a first decision on whether the difference data unit satisfies a first specific condition for a periodic-motion start decision;
when the first decision is positive, the processing unit recognizes the effective reference signal as the candidate reference signal, and based on the motion type indicator, makes a second decision on whether the motion type indicator indicates one selected from the plurality of motion types; and
when the second decision is positive, the processing unit recognizes the first motion type as the second motion type based on the motion type indicator, and obtains a motion type code representing the first motion type.

11. The motion recognition device according to claim 10, wherein:
the second motion portion is later than the first motion portion;
the second motion characteristic value data unit portion includes a plurality of specific motion characteristic values;
the processing unit provides beforehand a characteristic function code data unit expressed based on a relationship among the plurality of specific motion characteristic values, wherein:
the characteristic function code data unit is associated with the candidate reference signal code, a first recognition value domain, and a second recognition value domain adjacent to the first recognition value domain; and
the first and the second recognition value domains respectively indicate a third motion type and a fourth motion type, each of which is included in the plurality of motion types; and
when the second decision is negative, the processing unit performs a calculation to generate a recognition value based on the characteristic function code data unit and the second motion characteristic value data unit portion, determines an effective recognition value domain in the first and the second recognition value domains that the recognition value belongs to, recognizes the first motion type as an effective motion type indicated by the effective recognition value domain, and obtains the motion type code corresponding to the effective recognition value domain.

12. A motion recognition method, comprising steps of:
generating a motion parameter signal structure in response to a first body motion occurring at a specific position on a user's body, wherein the first body motion belongs to a first motion type;
generating a specific position code representing the specific position on the user's body based on the motion parameter signal structure;
recognizing the specific position to determine an effective reference signal for recognition of the first motion type; and
providing a recognition device, wherein the recognition device is configured to have an orientation, a gravity direction and a body coordinate system used to determine the orientation, and is fastened at the specific position, wherein:
the specific position is selected from a plurality of different positions on the user's body;
the step of generating the motion parameter signal structure in response to the first body motion further comprises sub-steps of:
generating a sense signal associated with the body coordinate system in response to the first body motion, wherein the sense signal includes an accelerometer signal and a gyroscope signal; and processing the sense signal to generate the motion parameter signal structure including a fusion signal of the accelerometer signal and the gyroscope signal;

the predetermined direction is determined based on the specific position;

the predetermined direction and the gravity direction have a first angle therebetween;

the fusion signal is a signal of an estimated angle associated with the first angle; and the step of generating the specific position code comprises sub-steps of:

in this state, making a first decision on whether a trigger signal is detected; and when the first decision is positive, generating the specific position code based on the estimated angle.

13. The motion recognition method according to claim 12, the first motion type is one selected from a plurality of motion types;

the plurality of motion types are predetermined in relation to the specific position, and respectively have a plurality of principal motion axis directions in relation to the body coordinate system, wherein the plurality of principal motion axis directions are detected beforehand to generate a plurality of principal motion axis direction data units respectively corresponding to the plurality of principal motion axis directions; and obtaining a recognition reference data unit based on the specific position code, wherein:

the recognition reference data unit is predetermined based on the plurality of principal motion axis direction data units, and includes a candidate reference signal code data unit and a motion type indicator data unit;

the candidate reference signal code data unit includes a first candidate reference signal code representing a first candidate reference signal derived from the motion parameter signal structure;

the motion type indicator data unit includes a motion type indicator corresponding to the first candidate reference signal code; and the motion type indicator indicates one of an invalid motion type and a second motion type included in the plurality of motion types; and determining the first candidate reference signal based on the motion parameter signal structure and the first candidate reference signal code.

14. The motion recognition method according to claim 13, wherein:

the motion parameter signal structure includes a plurality of motion parameter signals;

the first body motion includes a first motion portion and a second motion portion adjacent to the first motion portion;

the first and the second motion portions respectively form a first motion cycle and a second motion cycle adjacent to the first motion cycle;

the motion parameter signal structure includes a first motion parameter signal structure portion and a second motion parameter signal structure portion respectively corresponding to the first and the second motion portions;

the first candidate reference signal includes a first candidate reference signal portion and a second candidate reference signal portion respectively corresponding to the first and the second motion portions;

the recognition reference data unit further includes a representative signal code representing a representative signal included in the plurality of motion parameter signals; and the recognition method further comprises steps of:

obtaining a first motion characteristic value data unit from the motion parameter signal structure based on the first candidate reference signal, wherein:

the first motion characteristic value data unit includes a first motion characteristic value data unit portion and a second motion characteristic value data unit portion respectively corresponding to the first and the second motion portions; and the step of obtaining the first motion characteristic value data unit further comprises sub-steps of:

obtaining the first motion characteristic value data unit portion from the first motion parameter signal structure portion based on the first candidate reference signal portion; and obtaining the second motion characteristic value data unit portion from the second motion parameter signal structure portion based on the second candidate reference signal portion;

generating a difference data unit based on the first and the second motion characteristic value data unit portions;

making a first decision on whether the difference data unit satisfies a first specific condition for a periodic-motion start decision;

when the first decision is positive, recognizing the effective reference signal as the first candidate reference signal, determining that the first body motion satisfies a predetermined periodic-motion start condition, and based on the motion type indicator, making a second decision on whether the motion type indicator indicates one selected from the plurality of motion types; and when the second decision is positive, based on the motion type indicator, recognizing the first motion type as the second motion type, and obtaining a motion type code representing the first motion type.

15. The motion recognition method according to claim 14, wherein:

the step of generating the difference data unit further comprises sub-steps of:

obtaining a representative extreme value deviation between the first and the second motion characteristic value data unit portions by comparing the first motion characteristic value data unit portion with the second motion characteristic value data unit portion;

determining the representative signal based on the motion parameter signal structure and the representative signal code, wherein:

the first motion characteristic value data unit portion includes a first motion characteristic value data unit sub-portion corresponding to the representative signal, and the first motion characteristic value data unit sub-portion has a first maximum value, a first minimum value, and a first difference between the first maximum value and the first minimum value; and the second motion characteristic value data unit portion includes a second motion characteristic value data unit sub-portion corresponding to the representative signal, and the second motion characteristic value data unit sub-portion has a second maximum value, a second minimum value, and a second difference between the second maximum value and the second minimum value; and obtaining a representative value difference from the first and the second differences, wherein the difference data unit includes the representative extreme value deviation and the representative value difference;

the first specific condition includes a first sub-condition and a second sub-condition;

the first sub-condition is that the representative extreme value deviation falls within a first predetermined value range; and the second sub-condition is that the representative value difference falls within a second predetermined value range.

16. The motion recognition method according to claim 15, further comprising steps of:

providing a first characteristic function code data unit beforehand by sensing a plurality of body motions occurring at the specific position, wherein:

the second motion portion is later than the first motion portion;

the second motion characteristic value data unit portion includes a plurality of specific motion characteristic values;

the first characteristic function code data unit is associated with the first candidate reference signal code and a first plurality of recognition value domains;

the first characteristic function code data unit is employed to indicate one of the first plurality of recognition value domains;

the first plurality of recognition value domains include a first recognition value domain, a second recognition value domain adjacent to the first recognition value domain, and a first confidence value domain between the first and the second recognition value domains;

the first and the second recognition value domains respectively indicate a third motion type and a fourth motion type, each of which is included in the plurality of motion types;

the plurality of body motions are divided into a plurality of motion groups respectively belonging to the plurality of motion types; and the first characteristic function code data unit represent a motion type cut function employed to indicate the one of the first plurality of recognition value domains, and is expressed based on a relationship among the plurality of specific motion characteristic values;

when the second decision is negative, performing a first calculation to generate a first recognition value based on the first characteristic function code data unit and the second motion characteristic value data unit portion, and making a third decision on whether the first recognition value belongs to one of the first and the second recognition value domains;

when the third decision is positive, determining an effective recognition value domain in the first and the second recognition value domains that the first recognition value belongs to, recognizing the first motion type as an effective motion type indicated by the effective recognition value domain, and obtaining the motion type code corresponding to the effective recognition value domain; and generating a motion measurement information associated with the first body motion based on the motion type code.

17. The motion recognition method according to claim 16, further comprising steps of:

providing beforehand a second characteristic function code data unit associated with the first candidate reference signal code and a second plurality of recognition value domains, wherein:

the second characteristic function code data unit is different from the first characteristic function code data unit, and is employed to indicate one of the second plurality of recognition value domains;

the second plurality of recognition value domains include a third recognition value domain, a fourth recognition value domain adjacent to the third recognition value domain, and a second confidence value domain between the third and the fourth recognition value domains;

the third and the fourth recognition value domains respectively indicate a fifth motion type and a sixth motion type, each of which is included in the plurality of motion types; and in a second specific condition, one of the third and the fourth recognition value domains at least partially overlaps with one of the first and the second recognition value domains; and when the third decision is negative, performing a second calculation to generate a second recognition value based on the second characteristic function code data unit and the second motion characteristic value data unit portion, and deciding whether the second recognition value belongs to one of the third and the fourth recognition value domains, thereby recognizing the first motion type.

18. The motion recognition method according to claim 14, wherein:

the candidate reference signal code data unit further includes at least a second candidate reference signal code representing at least a second candidate reference signal, wherein:

the second candidate reference signal code represents the second candidate reference signal derived from the motion parameter signal structure; and the first candidate reference signal and the at least a second candidate reference signal constitute a candidate reference signal combination; and the recognition method further comprises steps of:

determining the at least a second candidate reference signal based on the motion parameter signal structure and the at least a second candidate reference signal code;

obtaining at least a second motion characteristic value data unit from the motion parameter signal structure based on the at least a second candidate reference signal, wherein the at least a second motion characteristic value data unit corresponds to the at least a second candidate reference signal; and when the first motion characteristic value data unit is processed, processing the at least a second motion characteristic value data unit to decide whether the candidate reference signal combination includes the effective reference signal.

* * * * *